(12) United States Patent
Hamilton et al.

(10) Patent No.: US 9,289,941 B2
(45) Date of Patent: Mar. 22, 2016

(54) APPARATUS AND METHOD FOR MAKING A LAYERED ELASTIC SUBSTRATE

(71) Applicant: The Procter & Gamble Company, Cincinnati, OH (US)

(72) Inventors: Raymond Scott Hamilton, Lebanon, OH (US); Mark Mason Hargett, Liberty Township, OH (US); Tina Brown, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 106 days.

(21) Appl. No.: 13/929,869

(22) Filed: Jun. 28, 2013

(65) Prior Publication Data

US 2014/0000795 A1    Jan. 2, 2014

Related U.S. Application Data

(60) Provisional application No. 61/665,942, filed on Jun. 29, 2012.

(51) Int. Cl.
*A61F 13/49*     (2006.01)
*B29C 55/02*     (2006.01)
(Continued)

(52) U.S. Cl.
CPC ......... *B29C 55/023* (2013.01); *A61F 13/15699* (2013.01); *B32B 37/144* (2013.01);
(Continued)

(58) Field of Classification Search
CPC ............ B65H 2801/57; B32B 2555/02; A61F 13/49011; A61F 13/49012; A61F 13/4902; A61F 13/49022; A61F 13/49023; A61F 13/49025; A61F 13/15601; A61F 13/15325; Y10T 156/1011; Y10T 156/1015; Y10T 156/1051; Y10T 156/1052

USPC .................................. 156/164, 229, 494, 495
See application file for complete search history.

(56) References Cited

U.S. PATENT DOCUMENTS 3,848,594 A    11/1974    Buell
3,860,003 A    1/1975     Buell
(Continued)

FOREIGN PATENT DOCUMENTS

EP          0 565 606 B1    3/1995
WO         WO 95/16746      6/1995
(Continued)

OTHER PUBLICATIONS

PCT/International Search Report, dated Nov. 6, 2013, 10 pages.
(Continued)

*Primary Examiner* — Carson Gross
(74) *Attorney, Agent, or Firm* — Sarah M. DeCristofaro; Abbey A. Lopez

(57) ABSTRACT

A method for making a layered elastic substrate includes advancing a first substrate layer and a second substrate layer in a machine direction. An elastic material is advanced in the machine direction in a stretched state. The elastic material may be bonded to the first substrate layer and the second substrate layer in a stretched state to form a layered elastic substrate. The layered elastic substrate may advance through a first metering device at speed, V1, and through a second metering device at speed, V2, subsequent to advancing through the first metering device, wherein V1 is greater than V2. As a result, the elastic material, and thus the layered elastic substrate, may be stretched to a first elongation at the first metering device and relaxed to a second elongation at the second device. The layered elastic substrate is cut and bonded to a continuous length of web material.

26 Claims, 22 Drawing Sheets

(51) Int. Cl.
  *B32B 37/14* (2006.01)
  *A61F 13/15* (2006.01)
(52) U.S. Cl.
  CPC ....... *A61F13/15601* (2013.01); *A61F 13/4902* (2013.01); *A61F 13/49011* (2013.01); *A61F 13/49012* (2013.01); *B32B 2555/02* (2013.01); *B65H 2801/57* (2013.01); *Y10T 156/1011* (2015.01); *Y10T 156/1015* (2015.01); *Y10T 156/1051* (2015.01); *Y10T 156/1052* (2015.01)

(56) References Cited

U.S. PATENT DOCUMENTS

| | | | |
|---|---|---|---|
| 3,911,173 | A | 10/1975 | Sprague, Jr. |
| 3,929,135 | A | 12/1975 | Thompson |
| 4,324,246 | A | 4/1982 | Mullane et al. |
| 4,342,314 | A | 8/1982 | Radel et al. |
| 4,381,781 | A | 5/1983 | Sciaraffa et al. |
| 4,463,045 | A | 7/1984 | Ahr et al. |
| 4,573,986 | A | 3/1986 | Minetola et al. |
| 4,609,518 | A | 9/1986 | Curro et al. |
| 4,610,678 | A | 9/1986 | Weisman et al. |
| 4,629,643 | A | 12/1986 | Curro et al. |
| 4,662,875 | A | 5/1987 | Hirotsu et al. |
| 4,673,402 | A | 6/1987 | Weisman et al. |
| 4,695,278 | A | 9/1987 | Lawson |
| 4,785,996 | A | 11/1988 | Ziecker et al. |
| 4,795,454 | A | 1/1989 | Dragoo |
| 4,808,178 | A | 2/1989 | Aziz et al. |
| 4,834,735 | A | 5/1989 | Alemany et al. |
| 4,842,666 | A | 6/1989 | Werenicz |
| 4,846,815 | A | 7/1989 | Scripps |
| 4,857,067 | A | 8/1989 | Wood et al. |
| 4,888,231 | A | 12/1989 | Angstadt |
| 4,894,060 | A | 1/1990 | Nestegard |
| 4,909,803 | A | 3/1990 | Aziz et al. |
| 4,925,520 | A * | 5/1990 | Beaudoin et al. ............. 156/494 |
| 4,946,527 | A | 8/1990 | Battrell |
| 4,963,140 | A | 10/1990 | Robertson et al. |
| 4,988,344 | A | 1/1991 | Reising et al. |
| 4,988,345 | A | 1/1991 | Reising |
| 5,006,394 | A | 4/1991 | Baird |
| 5,137,537 | A | 8/1992 | Herron et al. |
| 5,147,345 | A | 9/1992 | Young et al. |
| 5,151,092 | A | 9/1992 | Buell et al. |
| 5,221,274 | A | 6/1993 | Buell et al. |
| 5,260,345 | A | 11/1993 | Desmarais et al. |
| 5,342,338 | A | 8/1994 | Roe |
| 5,387,207 | A | 2/1995 | Dyer et al. |
| 5,518,801 | A | 5/1996 | Chappell et al. |
| 5,562,646 | A | 10/1996 | Goldman et al. |
| 5,571,096 | A | 11/1996 | Dobrin et al. |
| 5,580,411 | A | 12/1996 | Nease et al. |
| 5,595,567 | A | 1/1997 | King et al. |
| 5,624,427 | A | 4/1997 | Bergman et al. |
| 5,650,222 | A | 7/1997 | Desmarais et al. |
| 5,669,894 | A | 9/1997 | Goldman et al. |
| 5,674,216 | A | 10/1997 | Buell et al. |
| 5,691,035 | A | 11/1997 | Chappell et al. |
| 5,693,165 | A | 12/1997 | Schmitz |
| 5,723,087 | A | 3/1998 | Chappell et al. |
| 5,735,840 | A | 4/1998 | Kline et al. |
| 5,745,922 | A | 5/1998 | Rajala et al. |
| 5,865,823 | A | 2/1999 | Curro |
| 5,916,663 | A | 6/1999 | Chappell et al. |
| 5,928,212 | A | 7/1999 | Kline et al. |
| 5,941,864 | A | 8/1999 | Roe |
| 6,004,306 | A | 12/1999 | Roe et al. |
| 6,010,491 | A | 1/2000 | Roe et al. |
| 6,027,483 | A | 2/2000 | Chappell et al. |
| 6,251,097 | B1 | 6/2001 | Kline et al. |
| 6,414,215 | B1 | 7/2002 | Roe |
| 6,432,098 | B1 | 8/2002 | Kline et al. |
| 6,441,266 | B1 | 8/2002 | Dyer et al. |
| 6,554,815 | B1 * | 4/2003 | Umebayashi ............ 604/385.27 |
| 6,573,423 | B1 | 6/2003 | Herrlein et al. |
| 6,596,108 | B2 | 7/2003 | McCabe |
| 6,677,258 | B2 | 1/2004 | Carroll et al. |
| 7,569,039 | B2 | 8/2009 | Matsuda et al. |
| 7,648,771 | B2 * | 1/2010 | Day et al. ...................... 428/523 |
| 8,377,249 | B2 | 2/2013 | Gill |
| 2001/0025683 | A1 * | 10/2001 | Burriss et al. ................. 156/163 |
| 2004/0162536 | A1 | 8/2004 | Becker et al. |
| 2004/0167486 | A1 | 8/2004 | Busam et al. |
| 2005/0013975 | A1 * | 1/2005 | Brock et al. .................. 428/198 |
| 2005/0107764 | A1 | 5/2005 | Matsuda et al. |
| 2005/0215972 | A1 | 9/2005 | Roe et al. |
| 2005/0215973 | A1 | 9/2005 | Roe et al. |
| 2006/0083893 | A1 * | 4/2006 | Ashraf .......................... 428/131 |
| 2006/0135024 | A1 * | 6/2006 | Thomas et al. ............... 442/394 |
| 2006/0148358 | A1 * | 7/2006 | Hall et al. .................... 442/328 |
| 2006/0189956 | A1 | 8/2006 | Catalan |
| 2007/0078427 | A1 | 4/2007 | Raycheck et al. |
| 2007/0093769 | A1 | 4/2007 | Kline et al. |
| 2007/0142798 | A1 | 6/2007 | Goodlander et al. |
| 2007/0142806 | A1 | 6/2007 | Roe et al. |
| 2007/0219521 | A1 | 9/2007 | Hird et al. |
| 2007/0287348 | A1 | 12/2007 | Autran et al. |
| 2007/0287982 | A1 | 12/2007 | Lodge et al. |
| 2008/0132865 | A1 | 6/2008 | Li et al. |
| 2009/0099542 | A1 | 4/2009 | Thomas et al. |
| 2009/0294044 | A1 | 12/2009 | Gill |
| 2010/0252603 | A1 | 10/2010 | Gill |
| 2011/0094669 | A1 | 4/2011 | Oetjen |
| 2011/0139657 | A1 | 6/2011 | Hird et al. |
| 2011/0139658 | A1 | 6/2011 | Hird et al. |
| 2011/0139659 | A1 | 6/2011 | Hird et al. |
| 2011/0139662 | A1 | 6/2011 | Hird et al. |
| 2011/0152812 | A1 | 6/2011 | Hird et al. |
| 2012/0061015 | A1 | 3/2012 | LaVon et al. |
| 2012/0061016 | A1 | 3/2012 | LaVon et al. |
| 2012/0273129 | A1 | 11/2012 | Handziak |
| 2012/0330263 | A1 | 12/2012 | Lawson et al. |

FOREIGN PATENT DOCUMENTS

| | | |
|---|---|---|
| WO | WO 96/24319 A1 | 8/1996 |
| WO | WO 00/02727 A1 | 1/2000 |
| WO | WO 2006/015141 | 2/2006 |
| WO | WO 2009/146307 A1 | 12/2009 |

OTHER PUBLICATIONS

U.S. Appl. No. 13/929,854, filed Jun. 28, 2013, Mark Mason Hargett.
U.S. Appl. No. 13/929,878, filed Jun. 28, 2013, Raymond Scott Hamilton.

* cited by examiner

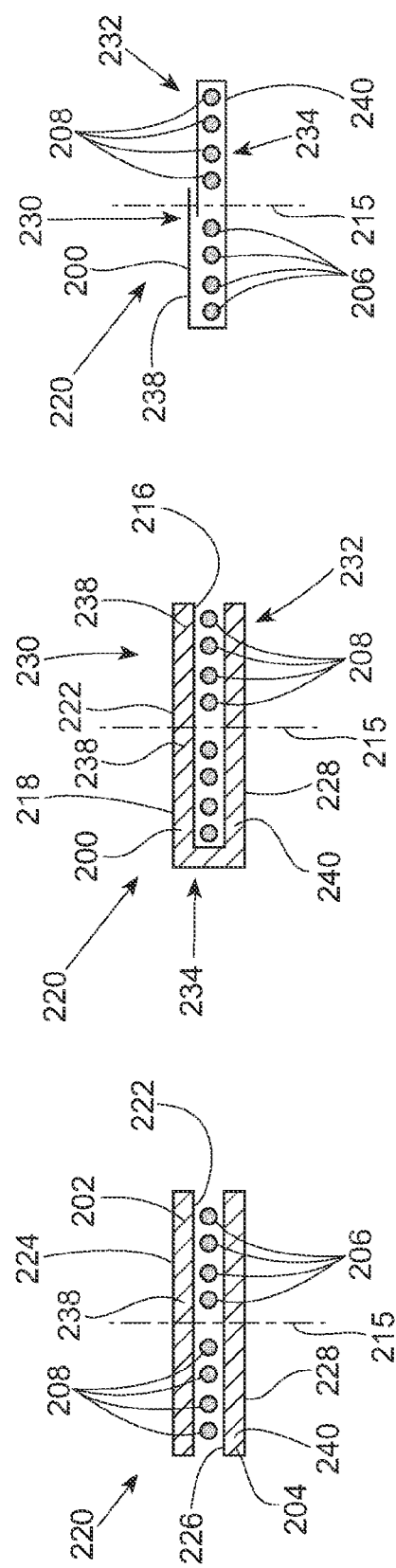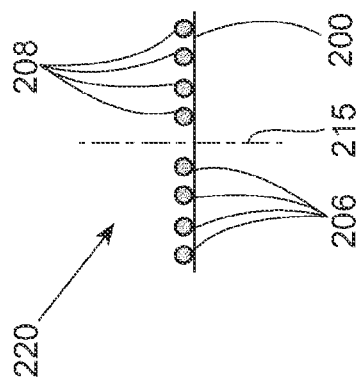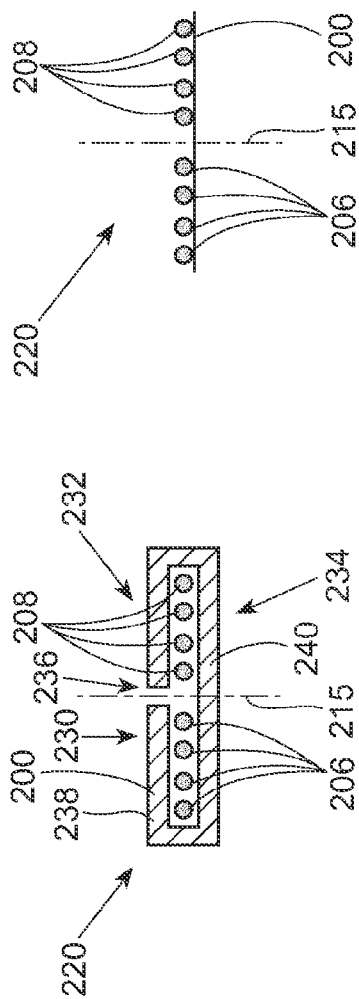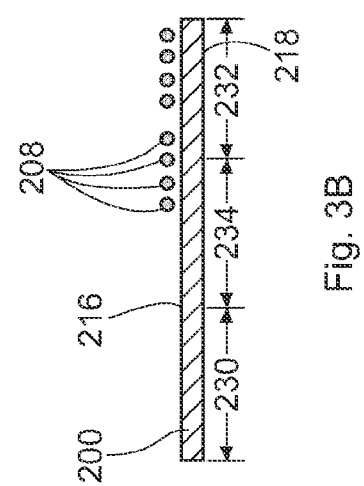

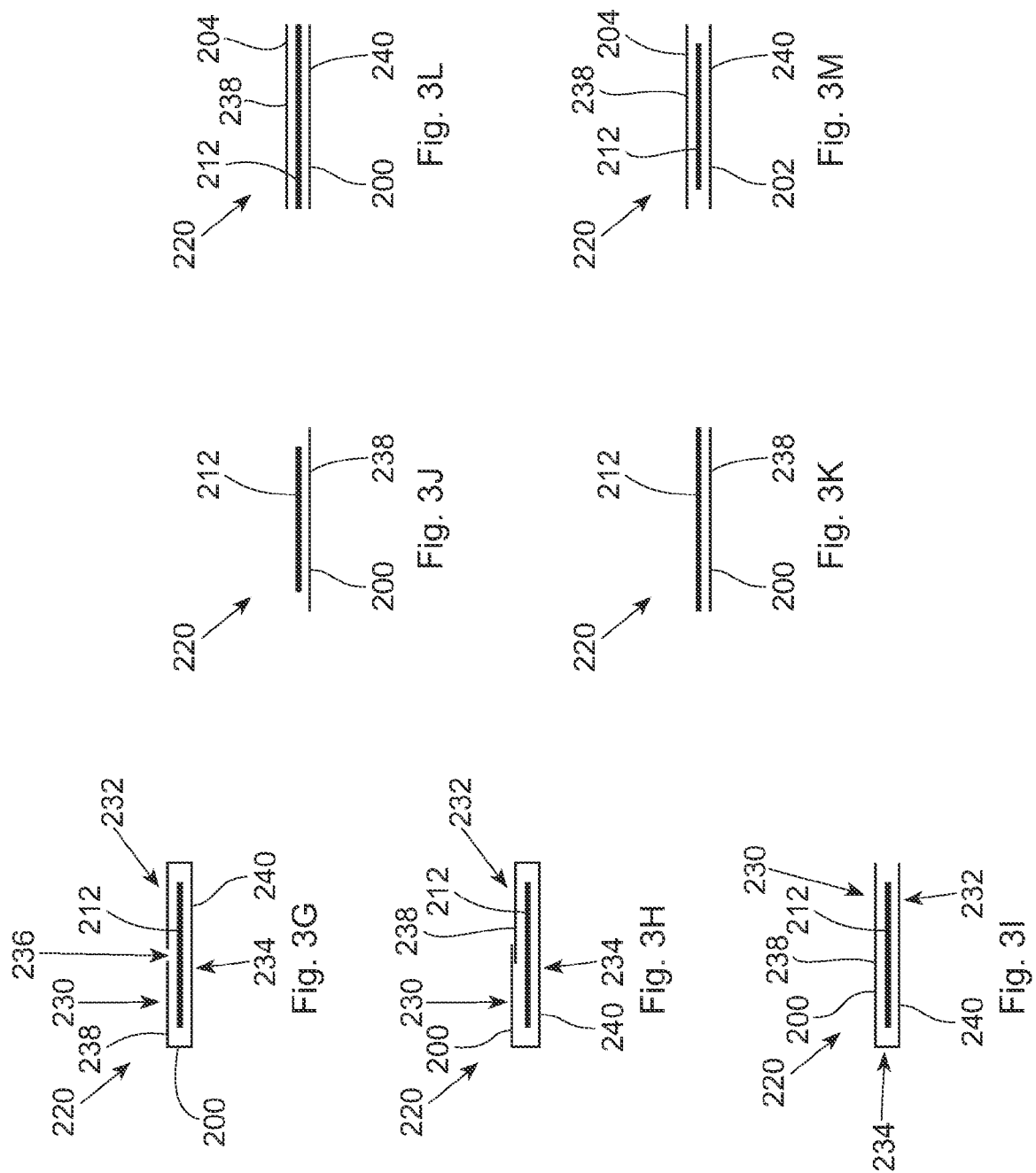

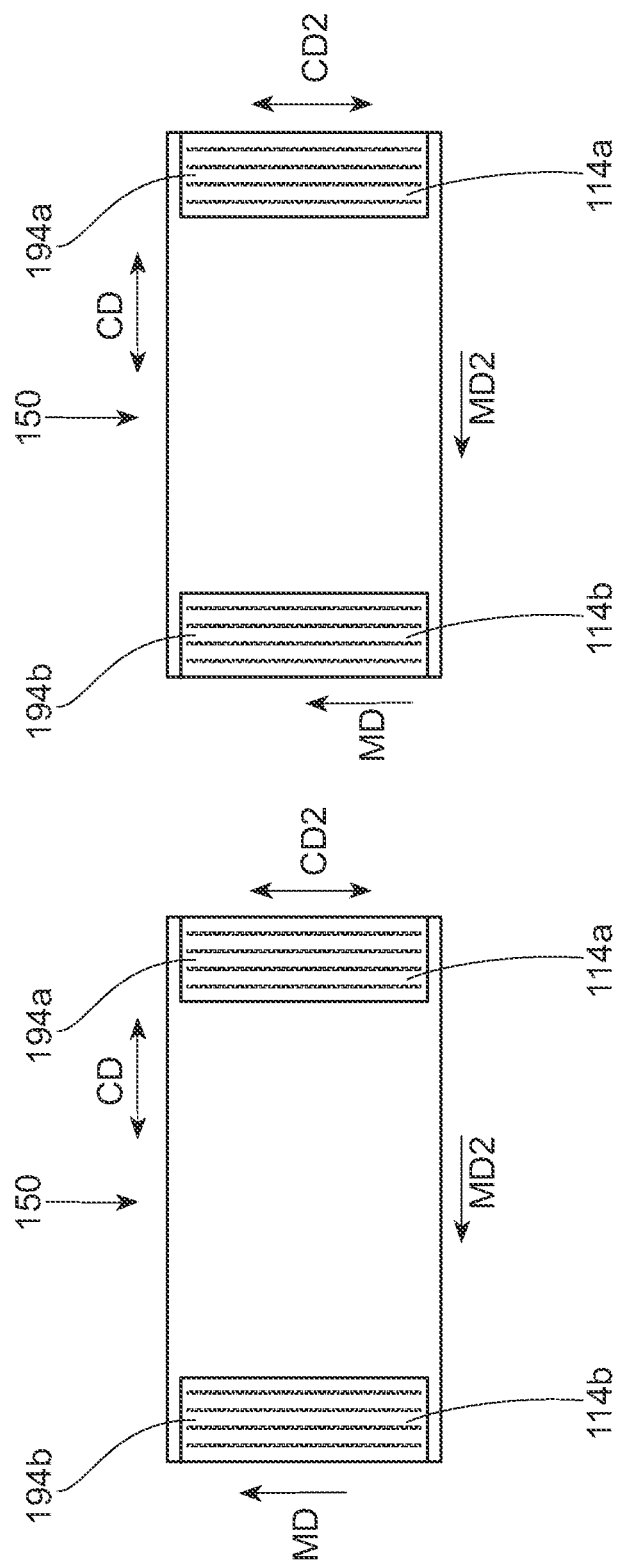

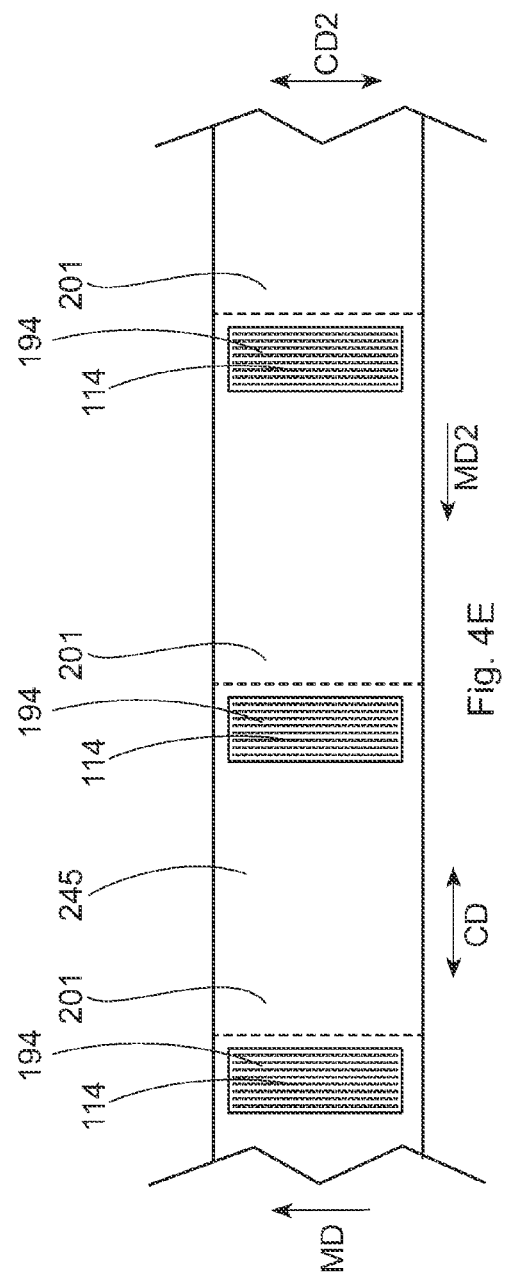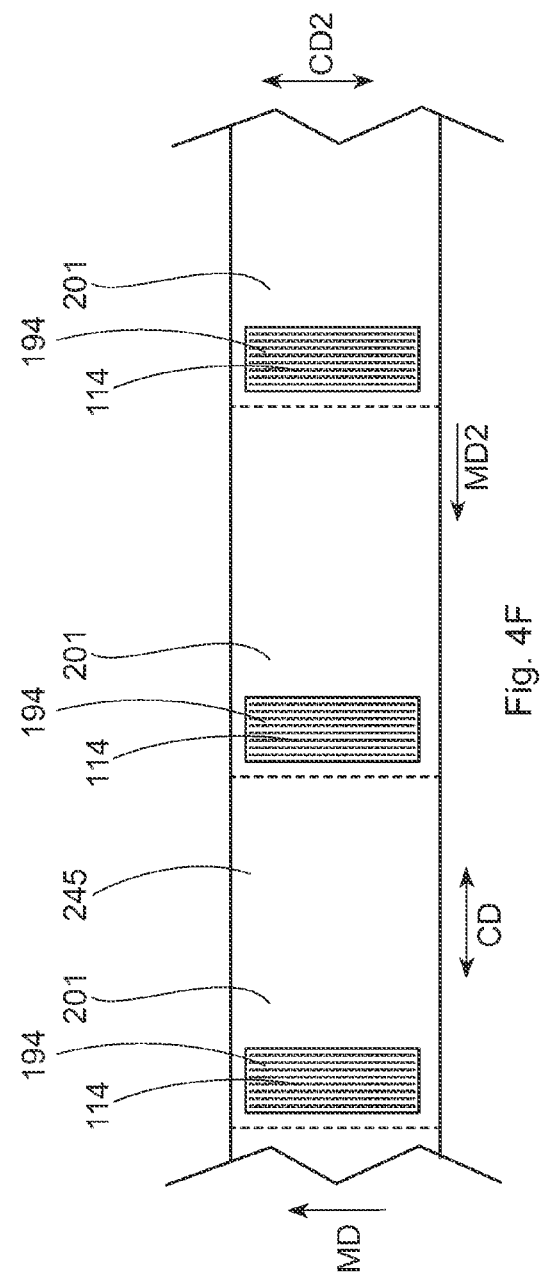

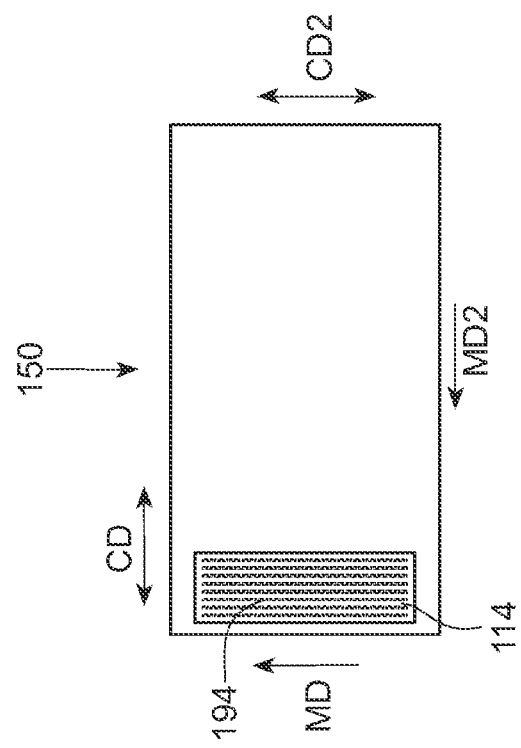
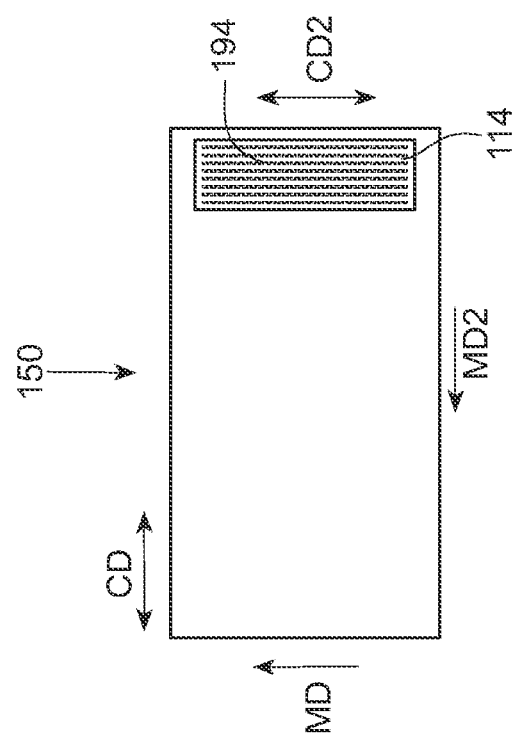

APPARATUS AND METHOD FOR MAKING A LAYERED ELASTIC SUBSTRATE

FIELD OF THE INVENTION

The present disclosure relates to methods for manufacturing absorbent articles, and more particularly, to apparatuses and methods for making discrete lengths of layered elastic substrates that may be used as components of absorbent articles.

BACKGROUND OF THE INVENTION

Along an assembly line, various types of articles, such as diapers and other absorbent articles, may be assembled by adding components to and/or otherwise modifying an advancing, continuous web of material. In some processes, advancing webs of material are combined with other advancing webs of material. In other processes, individual components created from advancing webs of material are combined with advancing webs of material, which in turn, are then combined with other advancing webs of material. In some cases, individual components created from advancing web(s) are combined with other individual components created from other advancing web(s). Webs of material and component parts used to manufacture diapers may include: backsheets, topsheets, leg cuffs, waistbands, absorbent core components, front and/or back ears, fastening components, and various types of elastic webs and components such as leg elastics, barrier leg cuff elastics, stretch side panels, and waist elastics. Once the desired component parts are assembled, the advancing web(s) and component parts are subjected to a final knife cut to separate the web(s) into discrete diapers or other absorbent articles.

In some instances, contraction around the waist of a wearer may improve the perceived fit of the absorbent article on the wearer. In some processes, discrete lengths of layered elastic substrates, such as waistbands, are bonded to absorbent articles to improve the perceived fit of the absorbent article. The waistbands may include an elastic material bonded to one or more layers of nonwoven substrate. The elastic material may include elastic films, ribbons, and/or strands. In some processes, the waistband may be formed by joining the nonwoven substrate with a plurality of elastic strands. In some processes, the elastic strands are stretched at full strain and joined to the nonwoven substrate. As a result, when the waistband is allowed to relax, gathers form in the waistband and the basis weight of the waistband increases such as shown in FIG. 1A. However, when the absorbent article is fully stretched, such as during application of the absorbent article to the wearer, the waistbands fully extend and flatten around the waist area as shown in FIG. 1B. As described more fully hereinafter, the basis weight of the waistband may also decrease. As a result, the flat, low basis weight waistband may negatively affect the real and/or perceived fit of the absorbent article. Therefore, it would be beneficial to have a method and apparatus for bonding a waistband to an absorbent article that is stretched below full strain such that the waistband continues to have gathers when the absorbent article is fully stretched.

SUMMARY OF THE INVENTION

In some aspects, the present disclosure relates to a method for making a layered elastic substrate. The method may comprise the steps of: advancing a substrate in a machine direction, the substrate defining a first edge region and a second edge region separated by an inner region along a cross direction, the substrate having a first surface and an opposing second surface; advancing an elastic material in a stretched state in the machine direction; bonding the elastic material in the stretched state to the first surface of the substrate; folding the substrate to position the first surface of the first edge region into a facing relationship with the first surface of the inner region; folding the substrate to position the first surface of the second edge region into a facing relationship with the first surface of the inner region to form a layered elastic substrate; advancing the layered elastic substrate through a first metering device at speed, V1; and advancing the layered elastic substrate through a second metering device at speed, V2, subsequent to advancing the layered elastic substrate through the first metering device, wherein V1 is greater than V2.

In some aspects, the method may comprise the steps of: advancing a first substrate layer in a machine direction, having a first surface and an opposing second surface; advancing a second substrate layer in the machine direction, having a first surface and an opposing second surface; advancing an elastic material in a stretched state in the machine direction; bonding the elastic material in the stretched state to the first surface of the first substrate layer and the first surface of the second substrate layer to form a layered elastic substrate; advancing the layered elastic substrate through a first metering device at speed, V1; and advancing the layered elastic substrate through a second metering device at speed, V2, subsequent to advancing the layered elastic substrate through the first metering device, wherein V1 is greater than V2.

In some aspects, the method may comprise the steps of: advancing a first substrate in a machine direction, having a first surface and an opposing second surface; advancing a second substrate in the machine direction, having a first surface and an opposing second surface; advancing an elastic material in a stretched state in the machine direction; bonding the elastic material in the stretched state to the first surface of the first substrate and the first surface of the second substrate to form a layered elastic substrate; stretching the elastic material to a first elongation at a first metering device; and consolidating the elastic material to a second elongation between the first metering device and a second metering device, wherein the first elongation is about 150% and the second elongation is about 80%.

BRIEF DESCRIPTION OF THE DRAWINGS

FIG. 3A is a schematic, sectional view of a layered elastic substrate with elastic strands.

FIG. 3B is a schematic, sectional view of a layered elastic substrate with elastic strands.

FIG. 3C is a schematic, sectional view of a layered elastic substrate with elastic strands.

FIG. 3D is a schematic, sectional view of a layered elastic substrate with elastic strands.

FIG. 3E is a schematic, sectional view of a layered elastic substrate with elastic strands.

FIG. 3F is a schematic, sectional view of a layered elastic substrate with elastic strands.

FIG. 3G is a schematic, sectional view of a layered elastic substrate with an elastic film.

FIG. 3H is a schematic, sectional view of a layered elastic substrate with an elastic film.

FIG. 3I is a schematic, sectional view of a layered elastic substrate with an elastic film.

FIG. 3J is a schematic, sectional view of a layered elastic substrate with an elastic film.

FIG. 3K is a schematic, sectional view of a layered elastic substrate with an elastic film.

FIG. 3L is a schematic, sectional view of a layered elastic substrate with an elastic film.

FIG. 3M is a schematic, sectional view of a layered elastic substrate with an elastic film.

FIG. 4D is a schematic, plan view of a discrete absorbent article having two discrete elastic waistbands taken along line 4D-4D of FIG. 4B.

FIGS. 4E and 4F are schematic, plan views of a continuous length of absorbent articles having discrete elastic waistbands.

FIGS. 4G and 4H are schematic, plan views of a discrete absorbent article having one discrete elastic waistband.

DETAILED DESCRIPTION OF THE INVENTION

Figure 1A:
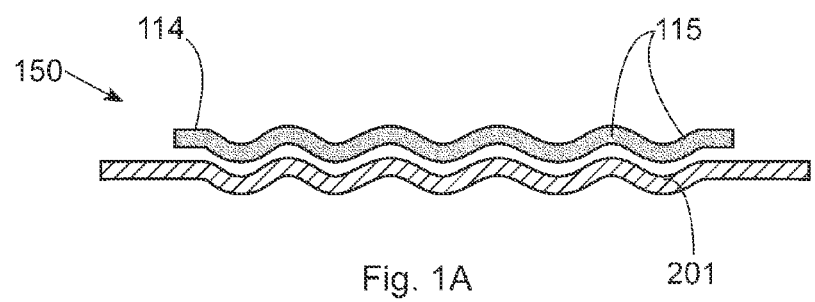
FIG. 1A is a sectional view of a prior art absorbent article in a relaxed state and having a discrete elastic waistband.
Figure 1B:
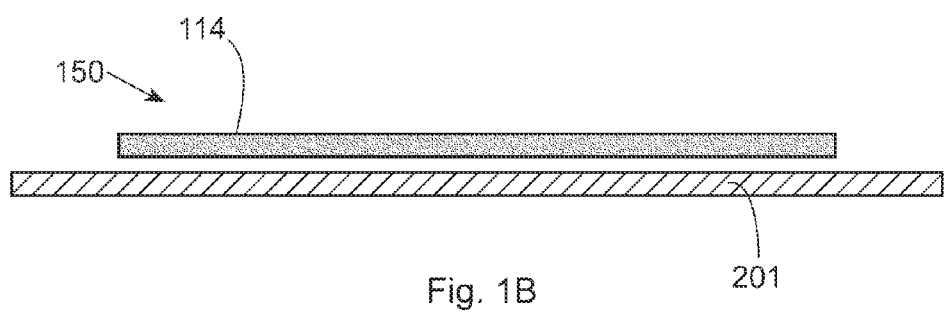
FIG. 1B is a sectional view of a prior art absorbent article in a fully stretched state and having a discrete elastic waistband.

This application claims priority to U.S. Provisional Application Ser. No. 61/665,942, filed Jun. 29, 2012, which is hereby incorporated by reference in its entirety.

The following definitions may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

"Longitudinal" means a direction running substantially perpendicular from a waist edge to a longitudinally opposing waist edge of an absorbent article when the article is in a flat out, uncontracted state, or from a waist edge to the bottom of the crotch, i.e. the fold line, in a bi-folded article. Directions within 45 degrees of the longitudinal direction are considered to be "longitudinal." "Lateral" refers to a direction running from a longitudinally extending side edge to a laterally opposing longitudinally extending side edge of an article and generally at a right angle to the longitudinal direction. Directions within 45 degrees of the lateral direction are considered to be "lateral."

"Substrate" is used herein to describe a material which is primarily two-dimensional (i.e. in an XY plane) and whose thickness (in a Z direction) is relatively small (i.e. 1/10 or less) in comparison to the material's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers bonded together. As such, a web is a substrate.

"Nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

"Machine direction" (MD) is used herein to refer to the direction of material flow through a process. In addition, relative placement and movement of material can be described as flowing in the machine direction through a process from upstream in the process to downstream in the process.

"Cross direction" (CD) is used herein to refer to a direction that is not parallel with, and usually perpendicular to, the machine direction.

"Radial" means a direction running from an axis of rotation of a drum toward an outer circumferential surface of the drum.

"Vacuum pressure" refers to a pressure applied to a discrete length of layered elastic substrate from radially inward from an outer circumferential surface of a drum. Vacuum pressure is a pressure below atmospheric air pressure.

"Stretchable" refers to materials that are capable of extending in at least one direction to a certain degree without undue rupture.

"Elastic," "elastomer" or "elastomeric" refers to any material that upon application of a force to the material's relaxed, initial length can stretch or elongate to an elongated length more than 10% greater than the material's initial length and will substantially recover back to about the material's initial length upon release of the applied force. The term "inelastic" refers herein to any material that does not fall within the definition of "elastic."

"Consolidation" and "consolidated" refers to a material undergoing a reduction in elongation from a first stretched length to a second stretched length that is less than the first stretched length and greater than zero.

"Relaxed state" defines a length of material when not stretched by an applied force.

"Stretched state" defines a length of material that is undergoing an increase in elongation as a result of an applied force.

In the context of the present description, an elongation of 0% refers to a material in relaxed state having a relaxed length of L, and elongation of 150% represents 2.5× the relaxed length, L, of the material. For example, an elastic strand having a relaxed length of 100 millimeters would have a length of 250 millimeters at 150% elongation. And an elastic strand having a relaxed length of 100 millimeters would have a length of 180 millimeters at 80% elongation.

The present disclosure relates to methods for assembling absorbent articles, and more particularly, to methods for making discrete lengths of layered elastic substrate in the form of elastic waistbands for absorbent articles. The layered elastic substrate may include a first substrate layer, a second substrate layer, and an elastic material located between the first substrate layer and the second substrate layer. During the process of making the layered elastic substrate, the elastic material may be advanced and stretched in a machine direction and may be joined with either or both the first and second substrate layers advancing in the machine direction. The elastic material, the first substrate layer, and the second substrate layer may advance, either together or separately, in the machine direction through a series of metering devices. For example, one metering device may be configured to stretch or consolidate the advancing elastic material before joining the elastic material with the first and second substrate layers. The same or a subsequent metering device may be used to join the elastic material with the first and second substrate layers to form the layered elastic substrate. In addition, metering devices may be used to consolidate the layered elastic substrate to a reduced elongation, thereby forming gathers in the layered elastic substrate. Once the layered elastic substrate is consolidated, the layered elastic substrate may be cut into discrete waistbands and bonded with a fully stretched, advancing continuous length of absorbent articles at the reduced elongation. As a result of consolidating the waistband prior to bonding the waistband to the fully stretched absorbent article, the waistbands may have gathers when the absorbent articles are fully extended.

It is to be appreciated that the layered elastic substrate can be formed in various ways. For example, in some exemplary configurations, the first continuous substrate layer may be formed from a first continuous substrate, and the second continuous substrate layer may be formed from a second continuous substrate. In other exemplary configurations, the first continuous substrate layer and/or the second continuous substrate layer may be formed by folding a portion of a single continuous substrate onto another portion of the single continuous substrate.

Although the methods and apparatuses herein are discussed below in the context of manufacturing discrete elastic waistbands for diapers, it is to be appreciated that the methods and apparatuses herein can be applied to other elastic components used on diapers as well as other types of absorbent articles. Other elastic components used on an absorbent article may include, for example, ears or side panels, leg cuffs, backsheets, and topsheets.

The methods and apparatuses discussed herein may be used to assemble layered elastic substrates with various configurations, some of which may be used in the manufacture of different types of absorbent articles. To help provide additional context to the subsequent discussion, the following provides a general description of absorbent articles in the form of diapers that include layered elastic substrates that may be assembled in accordance with the methods and apparatuses disclosed herein.

Figure 2:
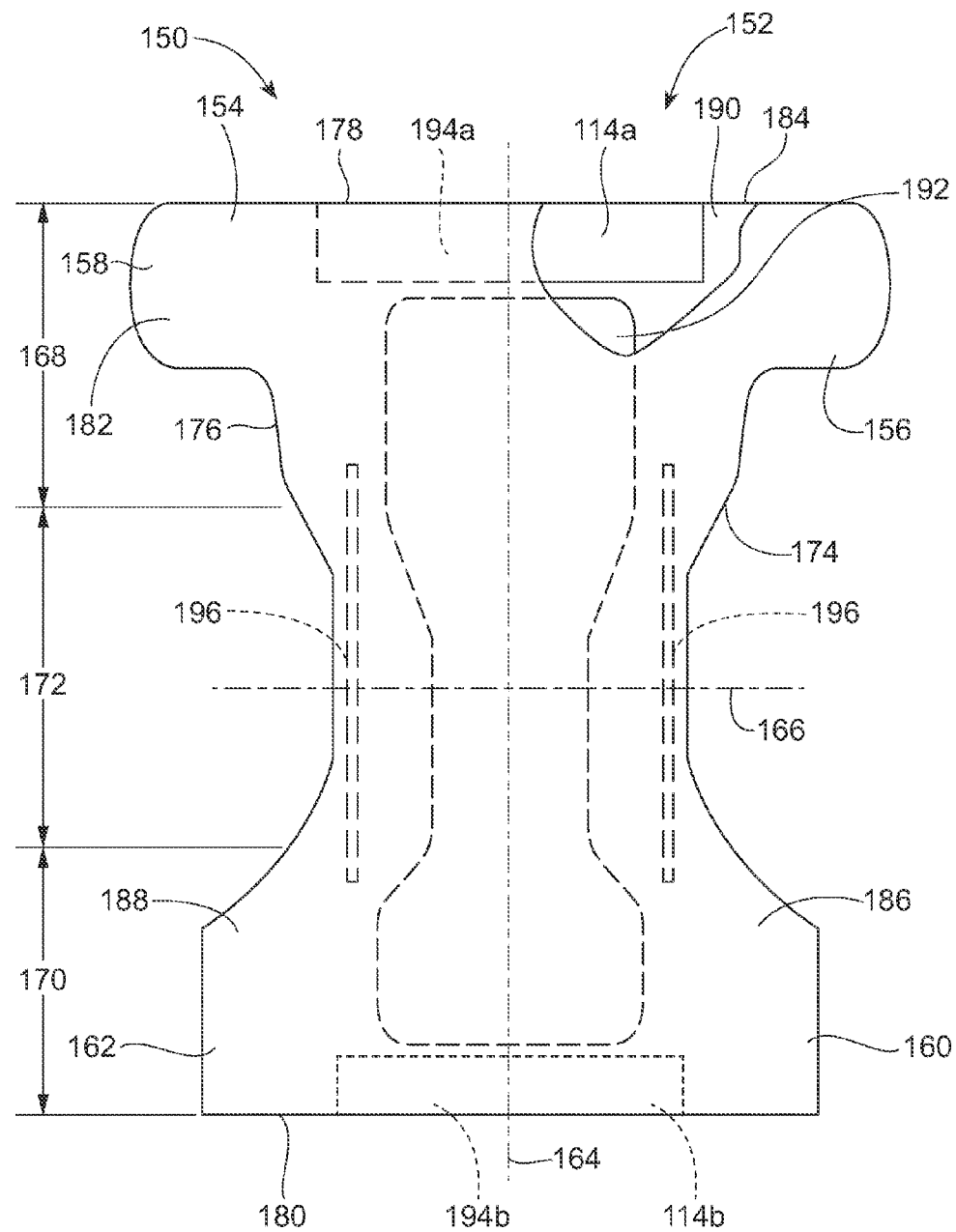
FIG. 2 is a partially cut-away, plan view of a disposable absorbent article having discrete elastic waistbands.

For the purposes of a specific illustration, FIG. 2 shows one example of a disposable absorbent article 150, such as described in U.S. Patent Publication No. US2008/0132865 A1, in the form of a diaper 152 that may be constructed from the methods and apparatuses disclosed herein. In particular, FIG. 2 is a plan view of one embodiment of a diaper 152 including a chassis 154 shown in a flat, unfolded condition, with the portion of the diaper 152 that faces a wearer oriented towards the viewer. A portion of the chassis structure is cut-away in FIG. 2 to more clearly show the construction of and various features that may be included in embodiments of the diaper.

As shown in FIG. 2, the diaper 152 includes a chassis 154 having a first ear 156, a second ear 158, a third ear 160, and a fourth ear 162. To provide a frame of reference for the present discussion, the chassis is shown with a longitudinal axis 164 and a lateral axis 166. The chassis 154 is shown as having a first waist region 168, a second waist region 170, and a crotch region 172 disposed intermediate the first and second waist regions. The periphery of the diaper is defined by a pair of longitudinally extending side edges 174, 176; a first outer edge 178 extending laterally adjacent the first waist region 168; and a second outer edge 180 extending laterally adjacent the second waist region 170. As shown in FIG. 2, the chassis 154 includes an inner, body-facing surface 182, and an outer, garment-facing surface 184. As shown in FIG. 2, the chassis 154 of the diaper 152 may include an outer covering layer 186 including a topsheet 188 and a backsheet 190. An absorbent core 192 may be disposed between a portion of the topsheet 188 and the backsheet 190. As discussed in more detail below, one or more of the regions may be stretchable and may include an elastomeric material or layered elastic substrate as described herein. As such, the diaper 152 may be configured to adapt to a specific wearer's anatomy upon application and to maintain coordination with the wearer's anatomy during wear.

Although the first and second ears 156, 158 as well as the third and fourth ears 160, 162 shown in FIG. 2 are illustrated as being integrally formed with the chassis 154, it is to be appreciated that other embodiments may include ears that are discrete elements connected with the chassis. In some embodiments, the ears are configured to be stretchable. The ears may also include one or more fastener elements adapted to releasably connect with each other and/or other fastener elements on the chassis. A more detailed discussion of stretchable ears can be found in U.S. Pat. Nos. 4,857,067; 5,151,092; 5,674,216; 6,677,258; 4,381,781; 5,580,411; and 6,004,306. The ears may also include various geometries and arrangements of stretch zones or elements, such as discussed in U.S. Pat. Publication Nos. US2005/0215972A1 and US2005/0215973A1.

As shown in FIG. 2, the diaper 152 may include leg cuffs 196 that may provide improved containment of liquids and other body exudates. The leg cuffs 196 may be disposed in various ways on the diaper 152. For example, the leg cuffs 196 may be disposed on the outer, garment-facing surface 184 of the chassis 154; the inner, body-facing surface 182; or between the inner and outer facing surfaces 182 or 184. Leg cuffs 196 may also be referred to as leg bands, side flaps, barrier cuffs, or elastic cuffs. U.S. Pat. No. 3,860,003 describes a disposable diaper that provides a contractible leg opening having a side flap and one or more elastic members to provide an elasticized leg cuff (a gasketing cuff). U.S. Pat. Nos. 4,808,178 and 4,909,803 describe disposable diapers having "stand-up" elasticized flaps (barrier cuffs). U.S. Pat. Nos. 4,695,278 and 4,795,454 describe disposable diapers having dual cuffs, including gasketing cuffs and barrier cuffs.

The diaper may be provided in the form of a pant-type diaper or may alternatively be provided with a re-closable fastening system, which may include fastener elements in various locations to help secure the diaper in position on the wearer. For example, fastener elements may be located on the first and second ears and may be adapted to releasably connect with one or more corresponding fastening elements located in the second waist region. It is to be appreciated that various types of fastening elements may be used with the diaper. In one example, the fastening elements include hook & loop fasteners, such as those available from 3M or Velcro Industries. In other examples, the fastening elements include adhesives and/or tap tabs, while others are configured as a macrofastener or hook (e.g., a MACRO or "button-like" fastener). Some exemplary fastening elements and systems are disclosed in U.S. Pat. Nos. 3,848,594; 4,662,875; 4,846,815; 4,894,060; 4,946,527; 5,151,092; and 5,221,274. Additional examples of fasteners and/or fastening elements are discussed in U.S. Pat. Nos. 6,251,097 and 6,432,098; and U.S. Patent Publication Nos. 2007/0078427 and 2007/0093769. Other fastening systems are described in more detail in U.S. Pat. Nos. 5,595,567; 5,624,427; 5,735,840; and 5,928,212. The fastening system may also provide a means for holding the article in a disposal configuration as disclosed in U.S. Pat. No. 4,963,140.

Components of the disposable absorbent article (i.e., diaper, disposable pant, adult incontinence article, sanitary napkin, pantiliner, etc.) described in this specification can at least partially be comprised of bio-sourced content as described in US 2007/0219521A1 Hird et al published on Sep. 20, 2007, US 2011/0139658A1 Hird et al published on Jun. 16, 2011, US 2011/0139657A1 Hird et al published on Jun. 16, 2011, US 2011/0152812A1 Hird et al published on Jun. 23, 2011, US 2011/0139662A1 Hird et al published on Jun. 16, 2011, and US 2011/0139659A1 Hird et al published on Jun. 16, 2011. These components include, but are not limited to, topsheet nonwovens, backsheet films, backsheet nonwovens, side panel nonwovens, barrier leg cuff nonwovens, super absorbent, nonwoven acquisition layers, core wrap nonwovens, adhesives, fastener hooks, and fastener landing zone nonwovens and film bases.

In at least one exemplary configuration, a disposable absorbent article component comprises a bio-based content value from about 10% to about 100% using ASTM D6866-10, method B, in another embodiment, from about 25% to about 75%, and in yet another embodiment, from about 50% to about 60% using ASTM D6866-10, method B.

In order to apply the methodology of ASTM D6866-10 to determine the bio-based content of any disposable absorbent article component, a representative sample of the disposable absorbent article component must be obtained for testing. In at least one embodiment, the disposable absorbent article component can be ground into particulates less than about 20 mesh using known grinding methods (e.g., Wiley® mill), and a representative sample of suitable mass taken from the randomly mixed particles.

The absorbent article may also include a first discrete length of layered elastic substrate 194a and a second discrete length of layered elastic substrate 194b such as shown in FIG. 2 in the form of first and second waistbands 114a and 114b. The first and second waistbands 114a and 114b may provide improved fit and waste containment. The first and second waistbands 114a and 114b may be located in the first waist region 168 and the second waist region 170, respectively. The first and second waistbands 114a and 114b may be configured to elastically expand and contract to dynamically fit the wearer's waist.

The first and second waistbands 114a and 114b can be incorporated into the diaper in accordance with the methods discussed herein. The first and second waistbands 114a and 114b may be positioned at least longitudinally outwardly from the absorbent core 192 and generally form at least a portion of the first and/or second outer edges 178, 180 of the diaper 152. In addition, the first and second waistbands 114a and 114b may extend laterally to include the ears. The first and second waistbands 114a and 114b may be disposed on the outer, garment-facing surface 184 of the chassis 154; the inner, body-facing surface 182; or between the inner and outer facing surfaces 182 and 184. It is to be appreciated that the first waistband 114a and the second waistband 114b shown in FIG. 2 may comprise the same materials and/or may have the same structure. While in other exemplary configurations, the first waistband 114a and the second waistband 114b may comprise different materials and/or may have different structures. The first and second waistbands 114a and 114b may be constructed in a number of different configurations including those described in U.S. Patent Publication Nos. 2007/0142806; 2007/0142798; 2007/0287983; and 2012/0330263.

The first and second waistbands 114a and 114b of FIG. 2 may be formed from a continuous length of layered elastic substrate 220. As discussed in more detail below and as shown in FIGS. 3A-3F, the layered elastic substrate 220 may be cut along cut line 215 to form the first waistband 114a and the second waistband 114b shown in FIG. 2. With reference to FIG. 3A, the layered elastic substrate 220 may include a first substrate layer 238 and a second substrate layer 240 separated by an elastic material 206 to form a layered elastic substrate 220. In some exemplary configurations, the first substrate layer 238 may be formed from a first continuous substrate 202 and the second substrate layer 240 may be formed from a second continuous substrate 204 such as shown in FIG. 3A. The elastic material 206 may be in the form of elastic strands 208. The first substrate 202 may be defined by a first surface 222 and an opposing second surface 224. The second substrate 204 may be defined by a first surface 226 and an opposing second surface 228. The elastic material 206 may be located between the first surface 222 of the first substrate 202 and the first surface 226 of the second substrate 204.

In some exemplary configurations, the first substrate layer 238 and/or the second substrate layer 240 of the layered elastic substrate 220 may be formed by folding a single continuous substrate 200 such as shown in FIGS. 3B-3E. The single continuous substrate 200 may be defined by a first edge region 230 and a second edge region 232 separated by a inner region 234, as well a first surface 216 and an opposing second surface 218. The first edge region 230 of the single continuous substrate 200 may be folded onto the second edge region 232 of the single continuous substrate 200 to form the first substrate layer 238 and the second substrate layer 240 as shown in FIG. 3C. In some exemplary configurations, the single continuous substrate 200 may be folded such that the first edge region 230 is proximate to the second edge region 232 so as to define a gap 236 between the first edge region 230 and the second edge region 232 such as shown in FIG. 3D. In some configurations, the first edge region 230 may abut the second edge region 232. In yet other exemplary configurations, the single continuous substrate 200 may be folded such that the first edge region 230 and the second edge region 232 overlap as shown in FIG. 3E. It is to be appreciated that the single continuous substrate 200 may be folded in various ways. As shown in FIG. 3F, in some exemplary configurations the layered elastic substrate 220 may include a first substrate layer 238 formed from a single continuous substrate 200. It is to be appreciated that the first and/or second continuous substrates 202 and 204 shown in FIG. 3A may also be folded into various configurations.

Figure 3N:
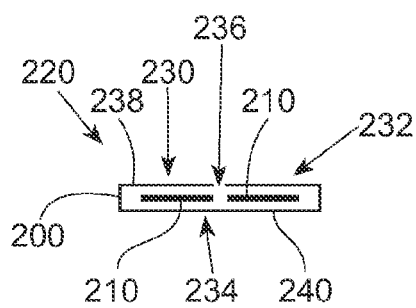
FIG. 3N is a schematic, sectional view of a layered elastic substrate with elastic ribbons.
Figure 3P:
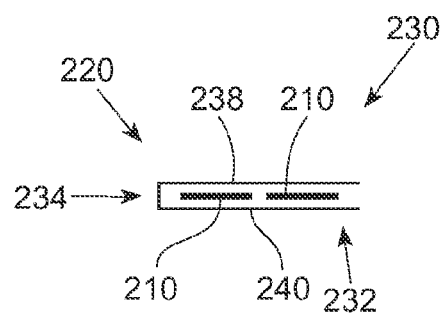
FIG. 3P is a schematic, sectional view of a layered elastic substrate with elastic ribbons.
Figure 3O:
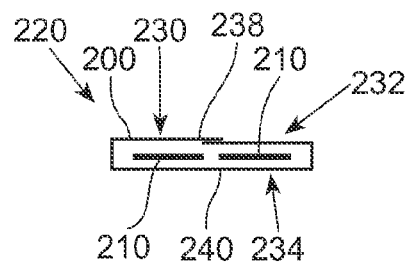
FIG. 3O is a schematic, sectional view of a layered elastic substrate with elastic ribbons.
Figure 3Q:
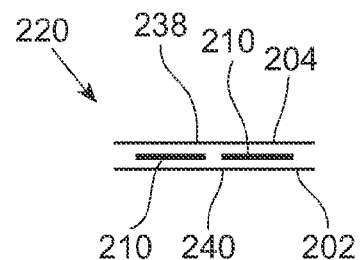
FIG. 3Q is a schematic, sectional view of a layered elastic substrate with elastic ribbons.

The elastic material 206 may be in the form of elastic strands 208, ribbons 210, films 212, or combinations thereof such as shown in FIGS. 3A-3Q. While it is shown in FIGS. 3A-3F that the layered elastic substrate 220 may include eight elastic strands 208, it is to be appreciated that the layered elastic substrate 220 may include various numbers of elastic strands 208. In some exemplary configurations, the layered elastic substrate 220 may include one or more elastic films 212 such as shown in FIGS. 3G-3M. In some exemplary configurations, the layered elastic substrate 220 may include one or more elastic ribbons 210 such as shown in FIGS. 3N-3Q. In some exemplary configurations, the elastic strands 208 and/or ribbons 210 may be longitudinally spaced at constant intervals. Or, in some exemplary configurations, the elastic strands 208 and/or ribbons 210 may be longitudinally spaced at different intervals. The elastic material 206 may have a decitex in the range of about 480 to about 1520. In some exemplary configurations, a layered elastic substrate 220 may comprise elastic materials 206 of various decitex values. It is to be appreciated that the elastic strands 208 may have various diameters and cross-sectional geometries.

Referring back to FIG. 2, in some exemplary configurations, the first waistband 114a may have a different configuration than the second waistband 114b. For example, the first waistband 114a may include a different number of elastic strands or ribbons than the second waistband 114b. In some exemplary configurations, the first waistband 114a may include elastic material of a different decitex than the elastic material of the second waistband 114b. It is to be appreciated that the first and second waistbands 114a and 114b may include various elastic materials configured in various ways. In some exemplary configurations, the first waistband 114a may include elastic strands of a different diameter and/or cross-sectional geometry than the elastic strands of the second waistband 114b.

It is to be appreciated that the layered elastic substrate may include various materials. For example, with regard to FIG. 3A, the first and/or second substrate layer 238 and 240 may include woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some exemplary configurations, the first and/or the second substrate layer 238 and 240 may include a polymeric film (e.g., polyethylene or polypropylene). In some exemplary configurations, the first and/or second substrate layers 238 and 240 may include a stretchable material.

Figure 4A:
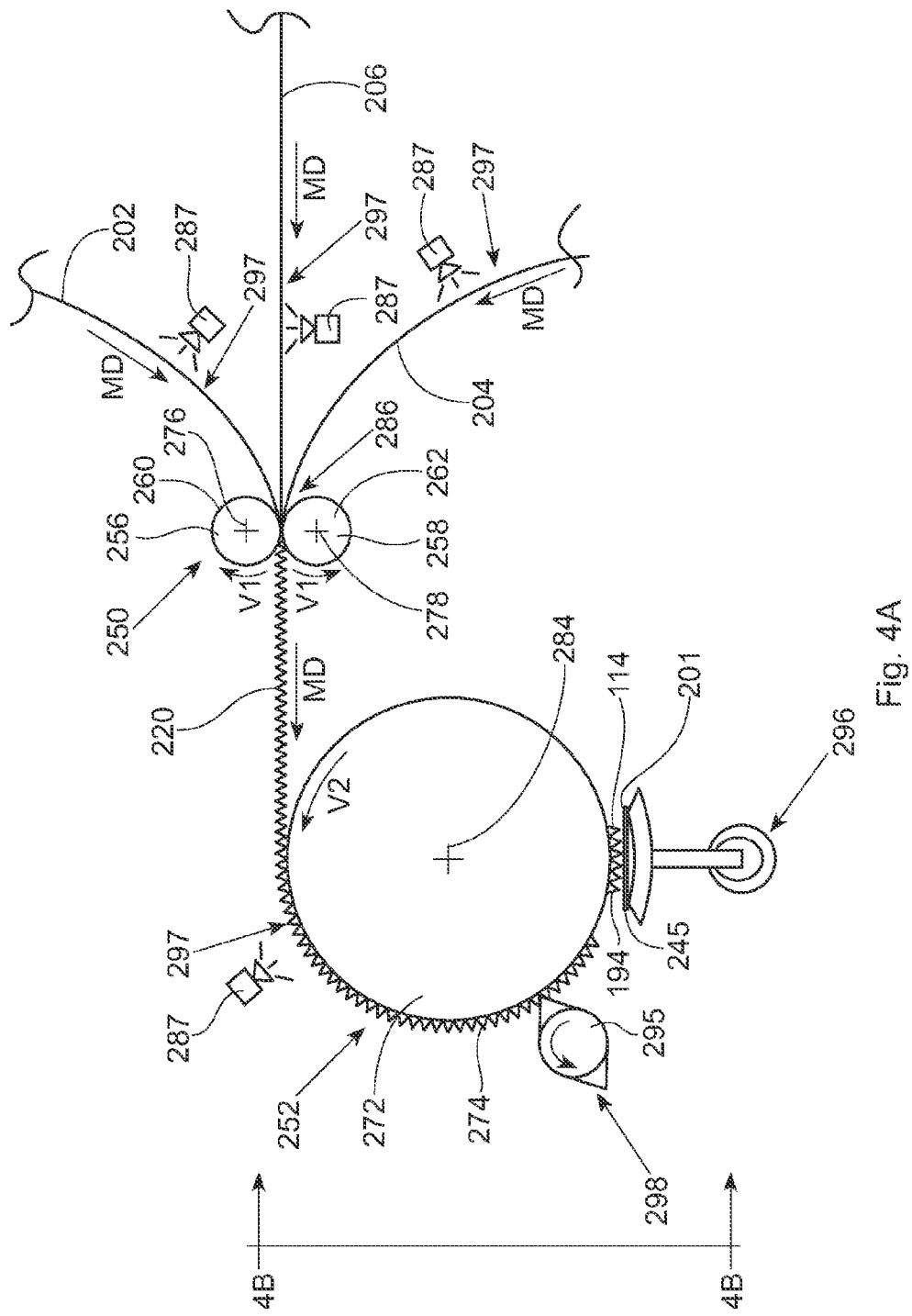
FIG. 4A is a schematic, side elevation view of an apparatus for making a layered elastic substrate, cutting the layered elastic substrate into discrete waistbands, and bonding the discrete waistbands with a continuous length of absorbent articles.
Figure 4B:
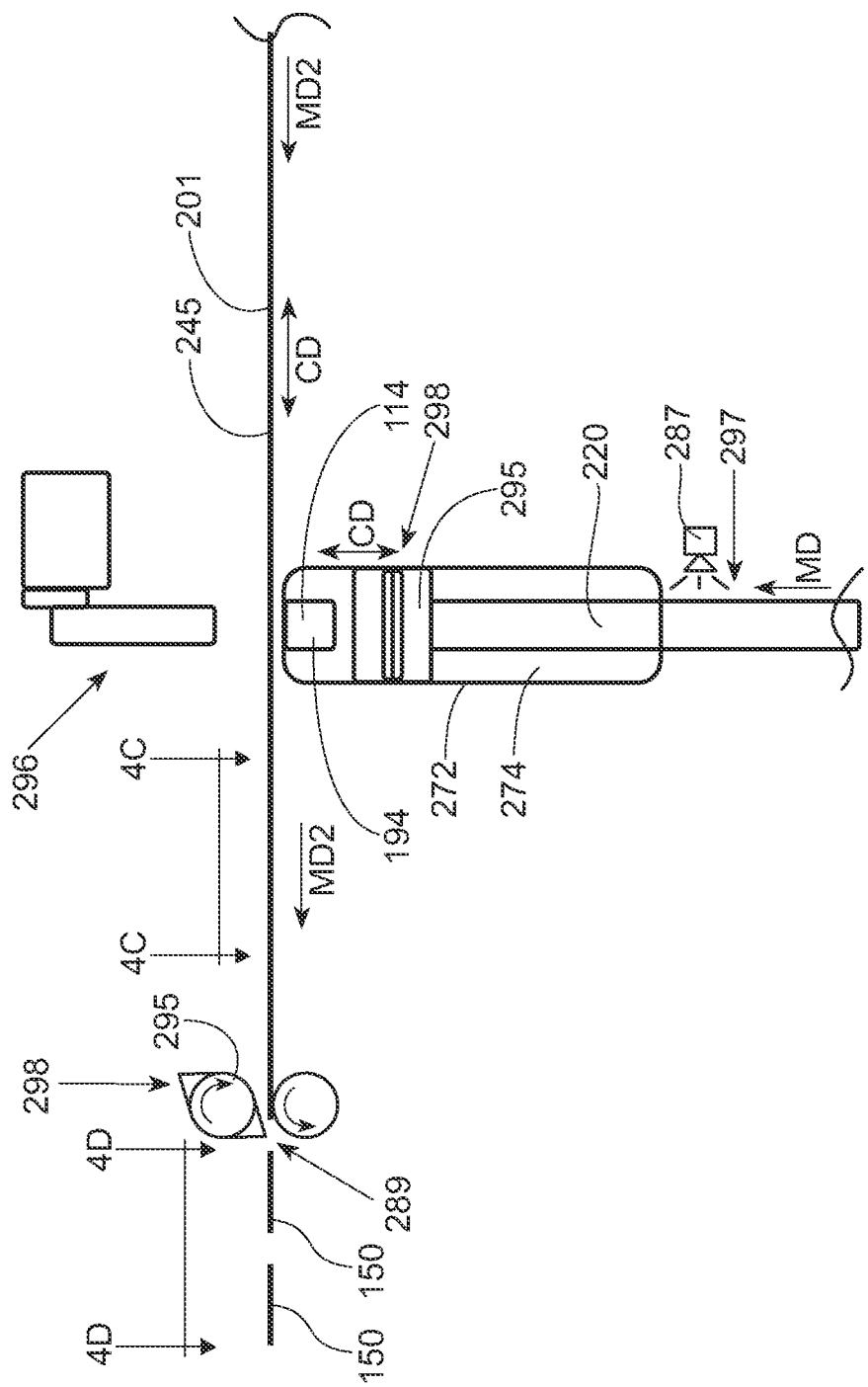
FIG. 4B is a schematic, side elevation view of an apparatus for bonding discrete elastic waistbands to a continuous length of absorbent articles taken along line 4B-4B of FIG. 4A.

As discussed above, the apparatuses and methods according to the present disclosure may be utilized to assemble discrete lengths of layered elastic substrate such as elastic waistbands for absorbent articles. It is to be appreciated that various methods and apparatuses may be used to assemble a layered elastic substrate. For example, FIGS. 4A and 4B show a process for forming discrete lengths of layered elastic substrate to be joined with absorbent articles. Although the following methods and apparatuses are provided in the context of the discrete absorbent article 150, it is to be appreciated that various absorbent articles can be manufactured according the methods disclosed herein, such as for example, the absorbent articles disclosed in U.S. Pat. Nos. 7,569,039 and 5,745,922; U.S. Patent Publication Nos. 2005/0107764A1, 2012/0061016A1, 2012/0061015A1, and US2012/0330263.

FIGS. 4A and 4B show an apparatus for forming and subsequently bonding discrete waistbands 114 to a continuous length of absorbent articles 201. As shown in FIG. 4A, a continuous length of elastic material 206 may be joined with continuous lengths of a first and second substrate 202 and 204 to form a layered elastic substrate 220. The layered elastic substrate 220 may advance onto a drum 272 to be cut into discrete lengths of layered elastic substrate 194, shown in the form of discrete waistbands 114. It is to be appreciated that FIG. 4B is a view taken along line 4B-4B of FIG. 4A. As shown in FIG. 4B, a continuous length of web material 245, shown in FIG. 4B as a continuous lengths of absorbent articles 201, may advance in a second machine direction MD2 and the discrete waistbands 114 may advance in the machine direction MD, which is also labeled as a second cross direction CD2 relative to the second machine direction MD2 of the advancing continuous length of absorbent articles 201. The elastic waistbands 114 may be intermittently bonded to the continuous length of absorbent articles 201 such that the elastic waistbands 114 are spaced apart on the continuous length of absorbent articles 201 in the second machine direction MD2. The continuous length of absorbent articles 201 may be combined with other components upstream or downstream of combining the discrete waistbands 114 with the absorbent articles 201.

It is to be appreciated that the continuous length of absorbent articles 201 may include various materials. For example, the continuous length of absorbent articles 201 may include topsheet material, backsheet material, or combinations thereof. The continuous length of absorbent articles 201 may be subjected to a final cut to create discrete absorbent articles 150 having first and second waistbands. An exemplary process for attaching elastic components to absorbent articles is described in U.S. Provisional Patent Application No. 61/665,930.

As shown in FIG. 4A, the continuous length of elastic material 206 is advanced in a machine direction MD in a stretched state and the continuous lengths of first and second substrates 202 and 204 are advanced in the machine direction MD to a first metering device 250. The elastic material 206 is joined with the first and second substrates 202 and 204 at the first metering device 250 to form a continuous layered elastic substrate 220. As shown in FIG. 4A, adhesive 297 may be applied to the first substrate 202, the second substrate 204, and the elastic material 206 using an adhesive applicator 287 before advancing through the first metering device 250. From the first metering device 250, the layered elastic substrate 220 may advance in the machine direction MD to a second metering device 252. As discussed in more detail below, the layered elastic substrate 220 may be consolidated between the first and second metering devices 250 and 252.

It is to be appreciated that the metering devices may be configured in various ways. For example, the first metering device 250 shown in FIG. 4A includes a first roller 256 having an outer circumferential surface 260 and rotates about a first axis of rotation 276 and a second roller 258 having an outer circumferential surface 262 and rotates about a second axis of rotation 278. The first roller 256 and the second roller 258 rotate in opposite directions, and the second roller 258 is adjacent the first roller 256 to define a first nip 286 between the first roller 256 and the second roller 258. The first and second rollers 256 and 258 rotate such that the outer circumferential surfaces 260 and 262 have a surface speed V1. The second metering device 252 shown in FIG. 4A includes a drum 272 having an outer circumferential surface 274 and rotates about an axis of rotation 284. The drum 272 rotates such that the outer circumferential surface 274 has a surface speed V2. Upstream of the first nip 286, the layered elastic substrate 220 may advance at a surface speed V1 or less. The layered elastic substrate 220 consolidates in the machine direction MD from the first elongation to a second elongation that is less than the first elongation because the layered elastic substrate 220 advances at surface speed V1 at the first nip 286 of the first metering device 250 and advances at surface speed V2 at the drum 272 of the second metering device 252, wherein V2 is less than V1. At the same time, the elastic material 206 consolidates from a first elongation to a second elongation that is less than the first elongation. As a result of consolidating the layered elastic substrate 220 to a reduced elongation, gathers form in the layered elastic substrate 220 between the first and second metering devices 250 and 252 as shown in FIG. 4A.

It is to be appreciated that various other apparatuses may be used for the metering devices. For example, the metering devices may include rollers, drums, conveyors, and combinations thereof. The metering devices may include one roller, drum, or conveyor. In some exemplary configurations, the first and second metering devices may include more than one roller, drum, conveyor, or combinations thereof.

With continuing reference to FIG. 4A, the metering devices may be used to consolidate the layered elastic substrate from a first elongation to a second elongation. The first elongation may be 150% and the second elongation may be 80%. It is to be appreciated that the methods and apparatuses disclosed herein may be used to consolidate a layered elastic substrate from a first elongation of various percentages to a second elongation of various percentages. For example, the first elongation may be 110%, 120%, 130%, 140%, 150%, 160%, 170%, 180%, 190%, or 200% and the second elongation may be 10%, 20%, 30%, 40%, 50%, 60%, 70%, 80%, 90%, 100%, 110%, 120%, 130%, 140%, or 150%.

Referring to FIGS. 4A and 4B, the layered elastic substrate 220 may be cut into discrete waistbands 114 and joined with an advancing continuous length of absorbent articles 201 advancing in the second machine direction MD2. The continuous length of layered elastic substrate 220 may advance onto and partially wrap around the outer circumferential surface 274 of the drum 272. A cutter 298, shown in FIGS. 4A and 4B as a knife roll 295 for the purpose of illustration, may be positioned adjacent to the outer circumferential surface 274 of the drum 272 to cut the layered elastic substrate 220 into discrete waistbands 114. As discussed in more detail below, the drum 272 may be configured with a vacuum system to hold the discrete waistbands 114 in a stretched state on the outer circumferential surface 274 of the drum 272 after being cut from the continuous layered elastic substrate 220.

Figure 5:
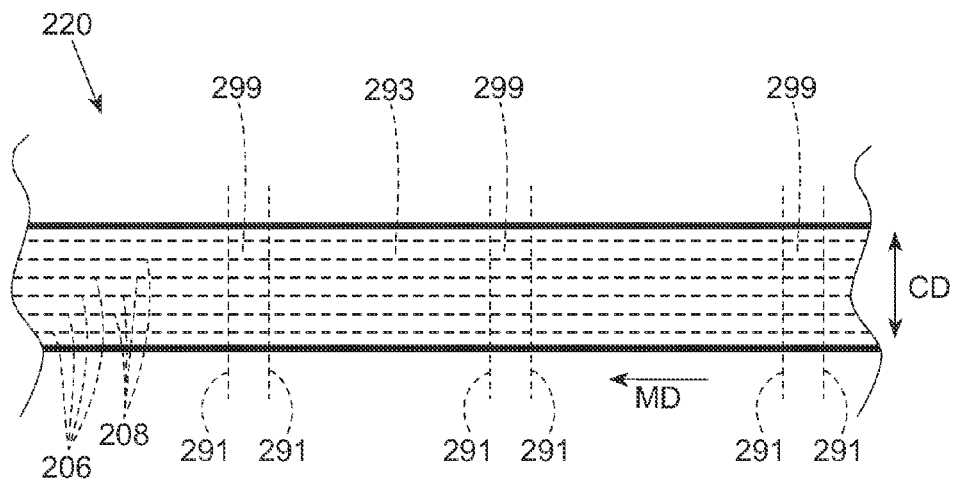
FIG. 5 is schematic, plan view of a continuous length of layered elastic substrate including an elastic material intermittently bonded to first and second substrate layers.
Figure 6A:
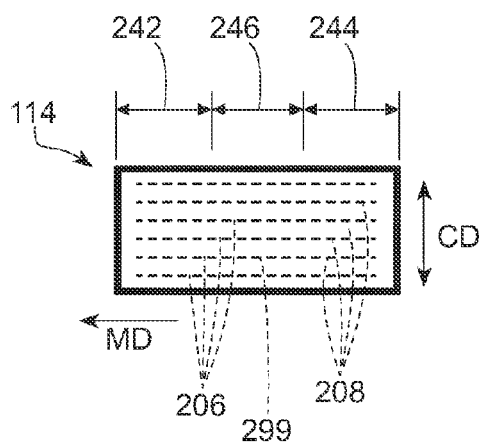
FIG. 6A is a schematic, plan view of a discrete waistband having an elastic material intermittently bonded to first and second substrate layers.
Figure 6B:
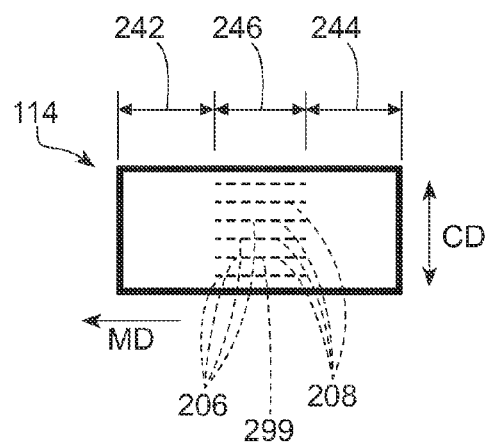
FIG. 6B is a schematic, plan view of a discrete waistband having an elastic material intermittently bonded to first and second substrate layers.
Figure 7:
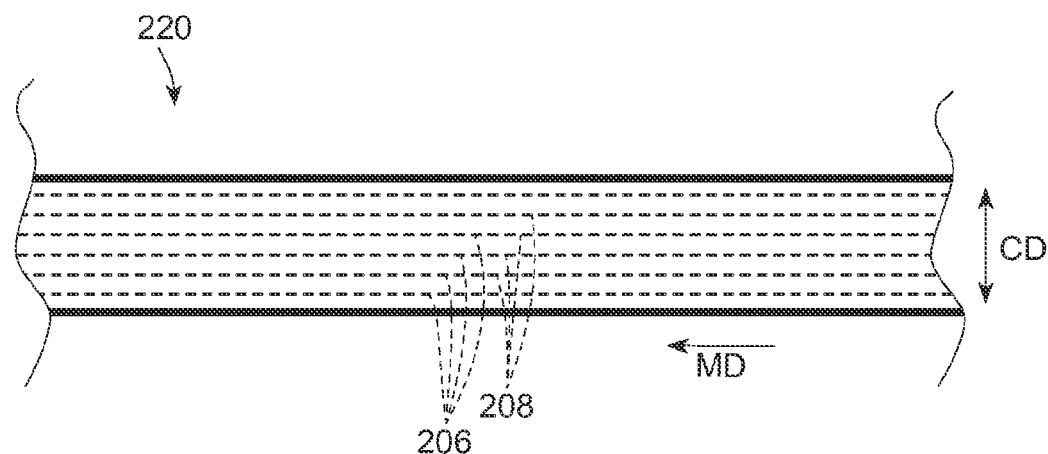
FIG. 7 is a schematic, plan view of a continuous length of layered elastic substrate including an elastic material that is continuously bonded to first and second substrates.
Figure 8:
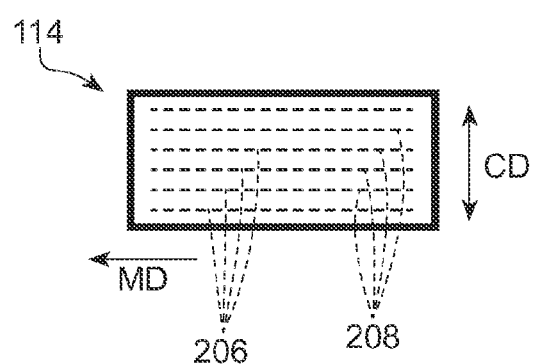
FIG. 8 is a schematic, plan view of a discrete waistband including an elastic material that is continuously bonded to the first and second substrate layers.

In some exemplary configurations, the elastic strands may retract after the layered elastic substrate is cut into discrete lengths of layered elastic substrate. As shown in FIG. 5, the elastic strands 208 may be intermittently bonded to the first and second substrates layers, forming bonded regions 293 and nonbonded regions 299 in the layered elastic substrate 220. With reference to FIGS. 4A, 4B, and 5, in this exemplary configuration, the cutter 298 may be configured to cut the layered elastic substrate 220 at the nonbonded regions 299 shown in FIG. 5. Consequently, as shown in FIG. 6A, the severed ends of the elastic strands 208 retract back to the bonded regions of the waistband 114. The waistband 114 may have a first end portion 242 and a second end portion 244 separated by an inner portion 246 as shown in FIGS. 6A and 6B. With reference to FIGS. 5, 6A, and 6B, in some exemplary configurations, the elastic material 206 may be intermittently bonded to the first and second substrate layers such that the elastic material 206 retracts back to the bonded regions located in the inner portion 246. As a result, there is no elastic material 206 located in the first and second end portions as shown in FIG. 6B. In other exemplary configurations, the elastic strands 208 may be continuously bonded to the first and second substrate 202 and 204 as shown in FIG. 7. In such an example, once the layered elastic substrate 220 is cut by the cutter 298 shown in FIGS. 4A and 4B, the elastic material 206 will extend the entire length of the waistband 114 as shown in FIG. 8.

Figure 4C:
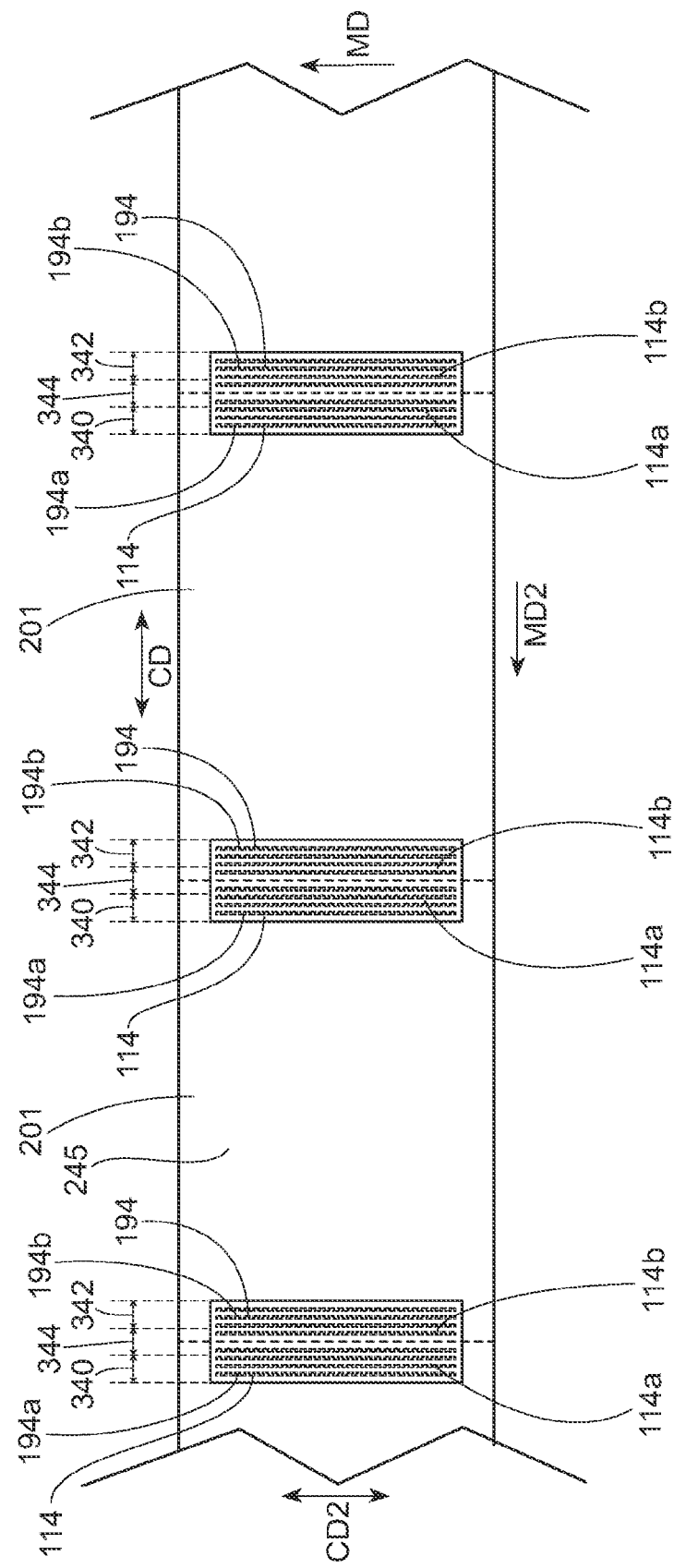
FIG. 4C is a schematic, plan view of a continuous length of absorbent articles having discrete elastic waistbands taken along line 4C-4C of FIG. 4B.

With reference back to FIGS. 4A and 4B, once the discrete waistbands 114 are cut from the layered elastic substrate 220, a tamper apparatus 296 may be used to bond the waistbands 114 to the continuous length of absorbent articles 201. Adhesive 297 may be applied to the discrete waistbands 114 using an adhesive applicator 287 before or while the waistbands 114 advance on the outer circumferential surface 274 of the drum 272. The tamper apparatus 296 may direct a portion of the continuous length of absorbent articles 201 into contact with the discrete waistband 114 advancing on the drum 272. Vacuum may be intermittently interrupted from the drum 272 to allow the discrete waistband 114 to release from the outer circumferential surface 274 of the drum 272. The discrete waistband 114 may bond to the continuous length of absorbent articles 201 in a stretched state. The tamper apparatus 296 may shift away from the drum 272 to allow the discrete waistband 114 to be removed from the drum 272. The continuous length of absorbent articles 201 then advances in the second machine direction MD2 and subsequent discrete waistbands 114 are bonded to the continuous length of absorbent articles 201 such that discrete waistbands 114 are spaced apart from each other discrete waistband 114 in the second machine direction MD2 as shown in FIG. 4C. An exemplary tamper apparatus is described in U.S. Provisional Patent Application No. 61/665,928.

As shown in FIG. 4B, the absorbent articles 201 having waistbands 114 may advance in the second machine direction MD2 through a nip 289 and be cut by a rotating knife roll 295 in the second cross direction CD2 into discrete absorbent articles 150. The waistbands 114 may be defined by a first edge region 340 and a second edge region 342 separated along the cross direction CD by an inner region 344 as shown in FIG. 4C. With reference to FIGS. 4C and 4D, the continuous length of absorbent articles 201 may be cut along the inner region 344 of the discrete waistbands 114, thereby forming a first waistband 114a on an absorbent article 150 and a second waistband 114b on a subsequently advancing absorbent article 150. It is to be appreciated that FIG. 4C is a view of taken along line 4C-4C of FIG. 4B and FIG. 4D is a view taken alone line 4D-4D of FIG. 4B. With reference to FIGS. 4E-4H, in some exemplary configurations, the continuous length of absorbent articles 201 may be cut adjacent to the waistband 114, either before or after the waistband 114, thereby creating an absorbent article 150 having only one waistband 114. It is to be appreciated that the absorbent articles may have waistbands arranged in various configurations.

Figure 9A:
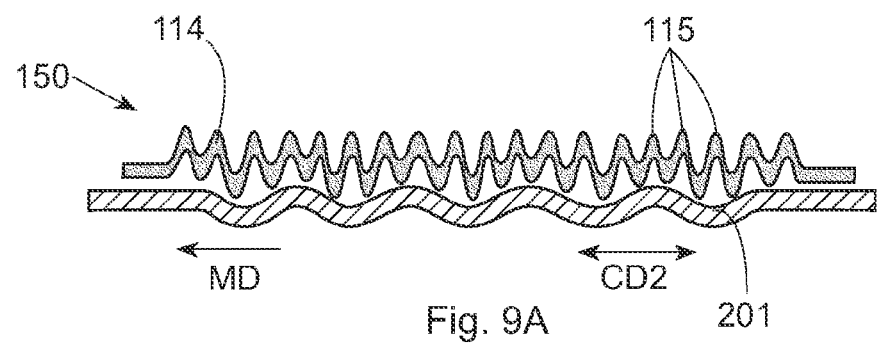
FIG. 9A is a sectional view of an absorbent article in a relaxed state and having a discrete elastic waistband.
Figure 9B:
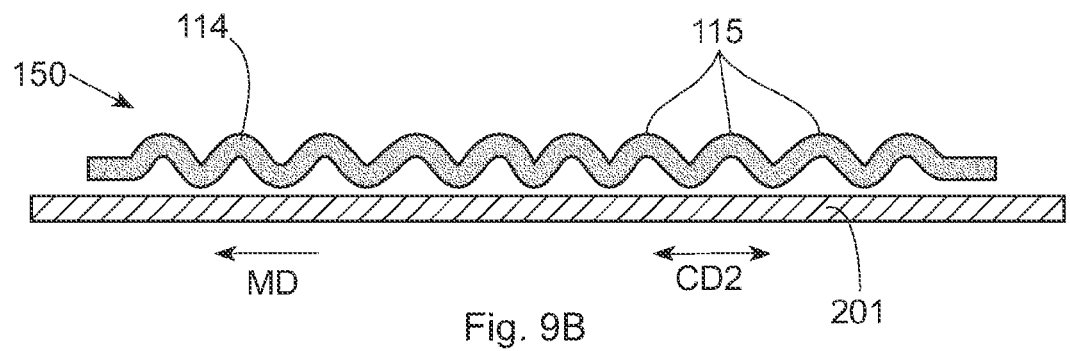
FIG. 9B is a sectional view of an absorbent article in a fully stretched state and having a discrete elastic waistband.

As a result of consolidating the layered elastic substrate and bonding the consolidated waistbands 114 to the absorbent articles 150 in a stretched state, gathers 115 form in the waistband 114 as shown in 9A and 9B. FIG. 9A shows a waistband 114 having gathers 115 when the absorbent article 150 is relaxed and FIG. 9B shows a waistband 114 having gathers 115 when the absorbent article is fully stretched. It is to be appreciated that as a result of bonding the waistband 114 to the fully stretched absorbent article 150 after the waistband 114 is consolidated to a reduced elongation, the waistband 114 has gathers 115 when the absorbent article 150 is fully stretched. With reference to FIGS. 1A, 1B, 9A, and 9B, it is to be appreciated that a waistband 114 with gathers 115 may have an increased basis weight compared with a waistband without gathers.

Figure 10:
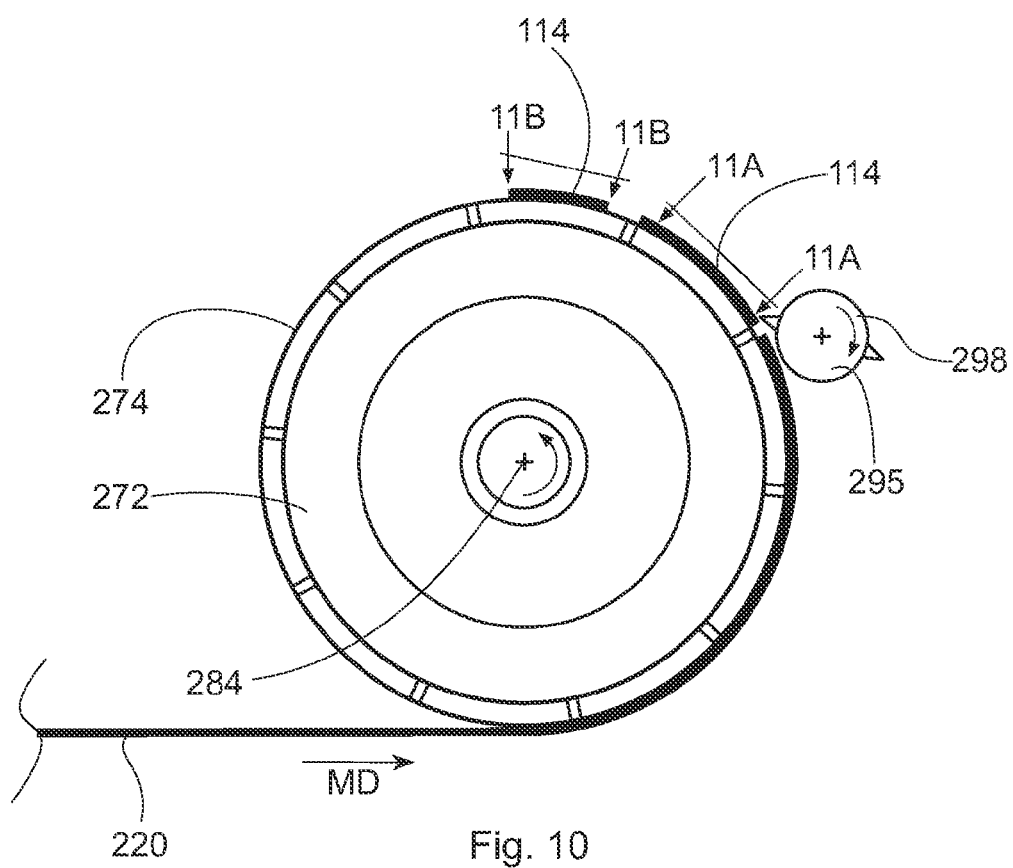
FIG. 10 is a schematic, side elevation view of an apparatus for cutting and consolidating discrete lengths of layered elastic substrate.
Figure 11A:
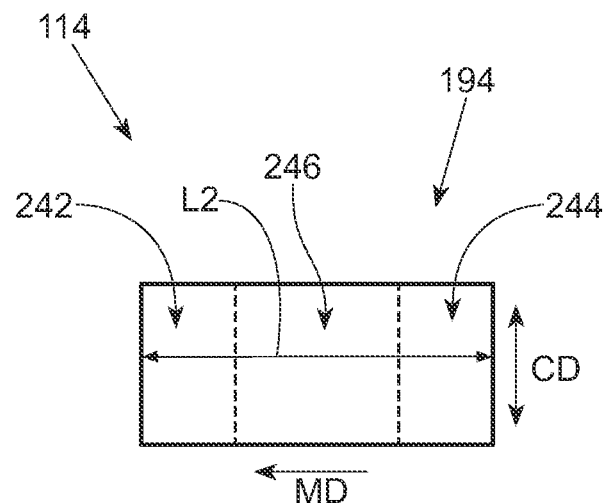
FIG. 11A is a schematic, plan view of a discrete waistband taken along line 11A-11A of FIG. 10.
Figure 11B:
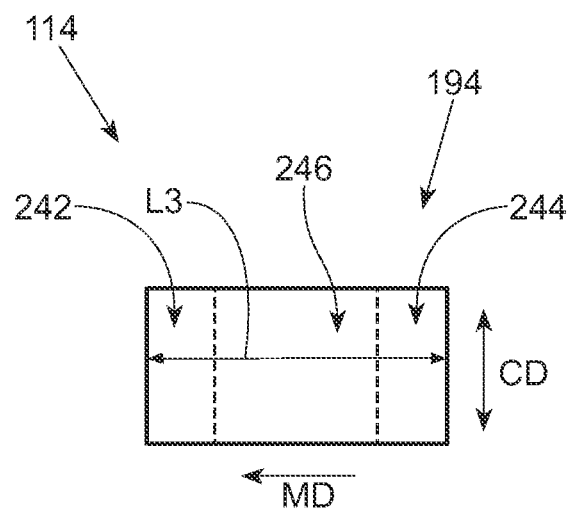
FIG. 11B is a schematic, plan view of a discrete waistband taken along line 11B-11B of FIG. 10.
Figure 11C:
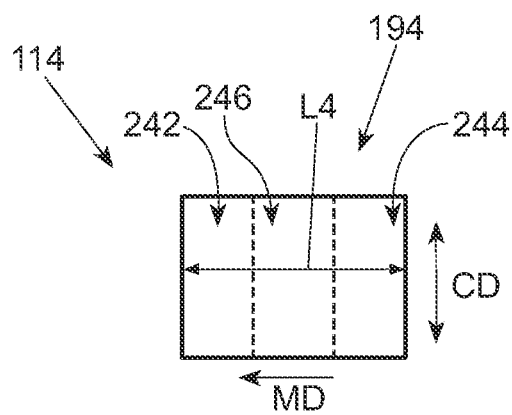
FIG. 11C is a schematic, plan view of a discrete waistband.
Figure 11D:
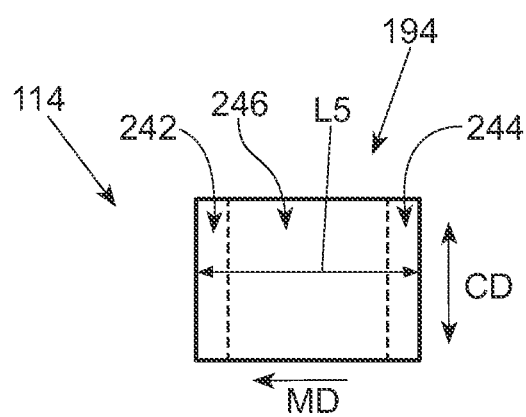
FIG. 11D is a schematic, plan view of a discrete waistband.

In some exemplary configurations, the discrete waistbands 114 may be further consolidated while advancing on the outer circumferential surface 274 of the drum 272 as shown in FIG. 10. With reference to FIGS. 10, 11A, and 11B, the waistbands 114 may have a first end portion 242 and a second end portion 244 separated along the ma by an inner portion 246. In some exemplary configurations, the drum 272 may be configured to increase the vacuum pressure, and thus decrease the vacuum force, applied to the first and second end portions 242 and 244 of the waistband 114 such that the waistband 114 consolidates from a second length L2 to a third length L3 as shown in FIG. 11B. As shown in FIG. 11B, the inner portion 246 may remain stretched while the first and second end portions 242 and 244 consolidate. It is to be appreciated that FIG. 11A is a view taken along line 11A-11A of FIG. 10 and FIG. 11B is a view taken along line 11B-11B of FIG. 10. In some exemplary configurations, vacuum pressure applied to the first end portion 242, second end portion 244, and the inner portion 246 of the discrete waistband 114 may be increased so that the first end portion 242, second end portion 244, and the inner portion 246 consolidate, and the waistband consolidates from a second length L2 to a fourth length L4 shown in FIG. 11C. In some exemplary configurations, vacuum pressure applied to the first and second end portions 242 and 244 may be increased such that the first and second end portions 242 and 244 relax and the waistband consolidates from a second length L2 to a fifth length L5 as shown in FIG. 11D. Methods and apparatuses for consolidating elastic substrates are described in U.S. Provisional Patent Application No. 61/665,933.

Figure 12:
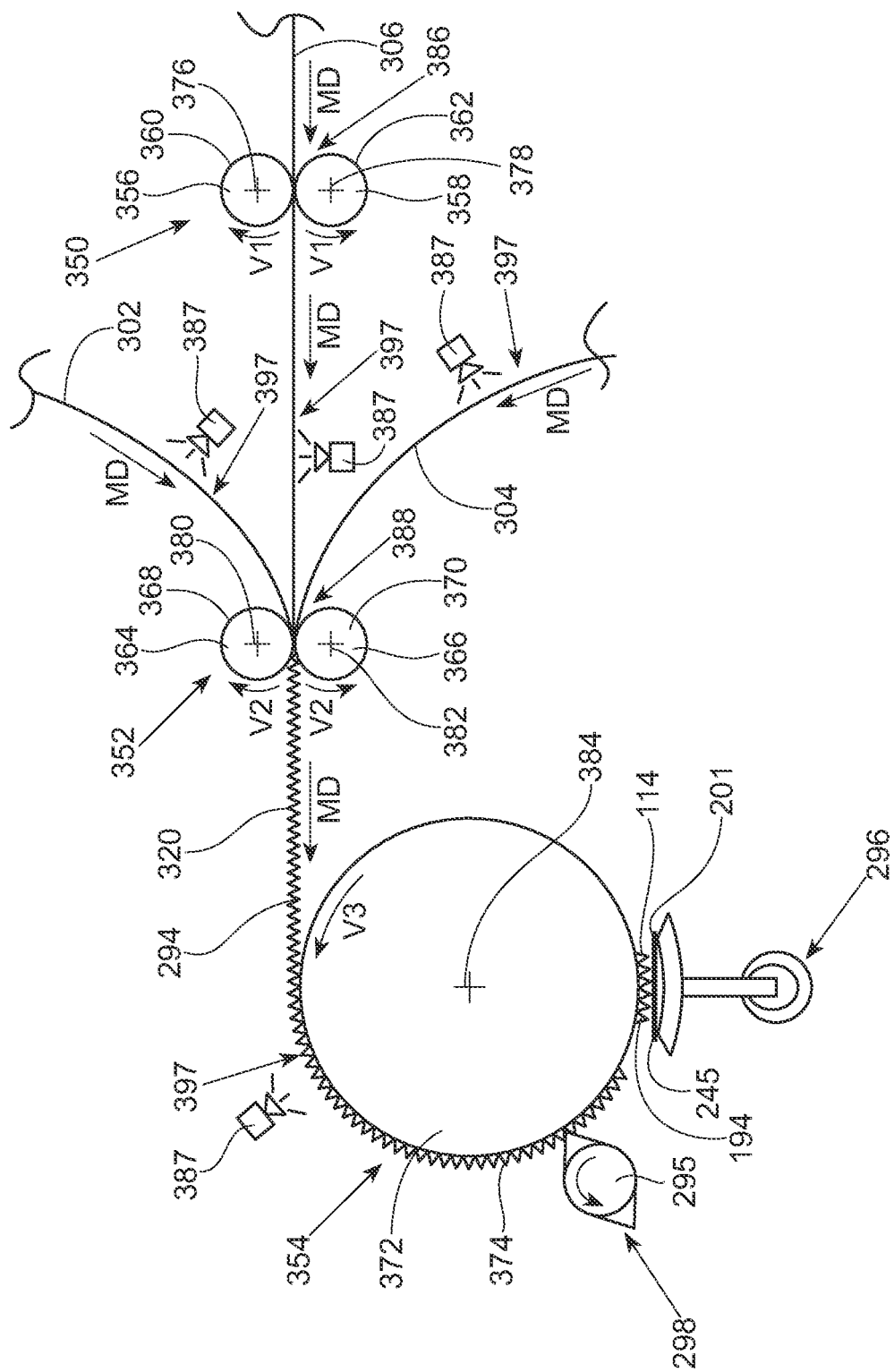
FIG. 12 is a schematic, side elevation view of an apparatus for making a layered elastic substrate, cutting the layered elastic substrate into discrete waistbands, and bonding the discrete waistbands with a continuous length of absorbent articles.

It is to be appreciated that various methods and apparatuses may be used for making discrete lengths of layered elastic substrates that are to be joined with absorbent articles according to the methods and apparatuses disclosed herein. For example, FIG. 12 shows another exemplary apparatus for assembling discrete lengths of layered elastic substrate 194. A continuous length of elastic material 306 may advance in a machine direction MD to a first metering device 350. The continuous length of elastic material 306 may then advance in the machine direction MD to a second metering device 352. The first and second metering devices 350 and 352 act to stretch the elastic material 306 along the machine direction MD between the first and second metering devices 350 and 352. A continuous length of first substrate 302 and a continuous length of second substrate material 304 are advanced in the machine direction MD. The elastic material 306 is combined with the first and second substrate 302 and 304 at the second metering device 352 to form a layered elastic substrate 320. As shown in FIG. 12, adhesive 397 may be applied to the first substrate 302, the second substrate 304, and the elastic material 306 using an adhesive applicator 387 before advancing through the second metering device 352. From the second metering device, the layered elastic substrate 320 may advance in the machine direction MD to a third metering device 354. The layered elastic substrate 320 consolidates between the second and third metering devices 352 and 354.

With continuing reference to FIG. 12, the first metering device 350 may include a first roller 356 having an outer circumferential surface 360 and rotates about a first axis of rotation 376 and a second roller 358 having an outer circumferential surface 362 and rotates about a second axis of rotation 378. The first roller 356 and the second roller 358 rotate in opposite directions, and the second roller 358 is adjacent the first roller 356 to define a first nip 386 between the first roller 356 and the second roller 358. The first and second rollers 356 and 358 rotate such that the outer circumferential surfaces 360 and 362 each have a surface speed V1. The second metering device 352 includes a first roller 364 having an outer circumferential surface 368 and rotates about a first axis of rotation 380 and a second roller 366 having an outer circumferential surface 370 and rotates about a second axis of rotation 382. The first roller 364 and the second roller 366 rotate in opposite directions, and the second roller 366 is adjacent the first roller 364 to define a second nip 388 between the first roller 364 and the second roller 366. The first and second rollers 364 and 366 rotate such that the outer circumferential surfaces 368 and 370 each have a surface speed V2. The surface speed V2 may be greater than the surface speed V1 such that the elastic material 306 stretches from a first elongation to a second elongation that is greater than the first elongation between the first metering device 350 and the second metering device 352. The third metering device 354 may include a drum 372 having an outer circumferential surface 374 and rotates about an axis of rotation 384. The drum 372 rotates such that the outer circumferential surface 374 has a surface speed V3. The surface speed V3 may be less than the surface speed V2, but greater than the surface speed V1, such that the layered elastic substrate 320 consolidates from a second elongation to a third elongation that is less than the second elongation and greater than the first elongation.

Figure 13:
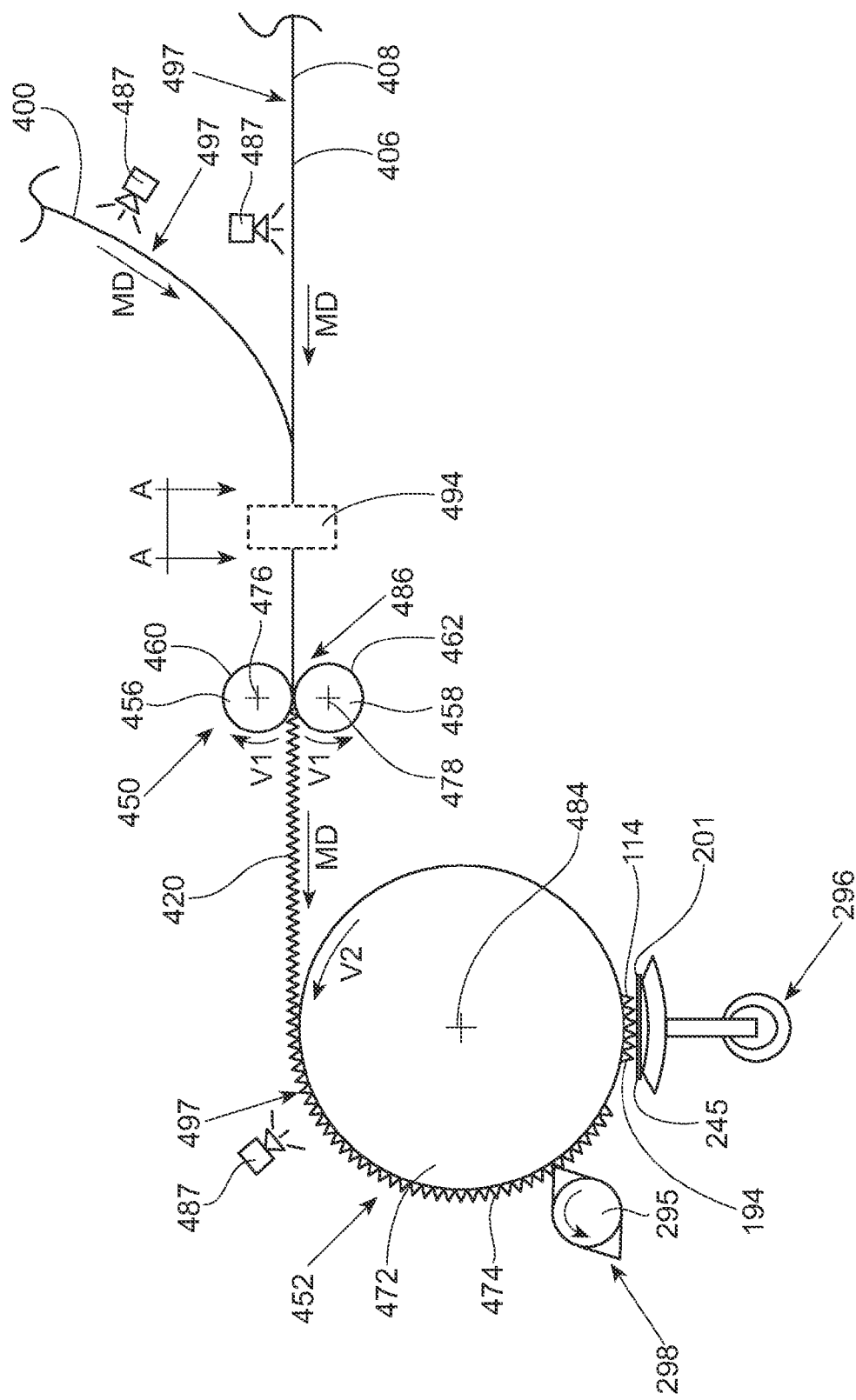
FIG. 13 is a schematic, side elevation view of an apparatus for making a layered elastic substrate, cutting the layered elastic substrate into discrete waistbands, and bonding the discrete waistbands with a continuous length of absorbent articles.

FIG. 13 shows another exemplary apparatus for assembling discrete lengths of layered elastic substrate. As shown in FIG. 13, a continuous length of elastic material 406, shown in the form of elastic strands 408 for exemplary purpose only, may advance in a stretched state in a machine direction MD and a single continuous substrate 400 may advance in a machine direction MD. The single continuous substrate 400 may be folded over the elastic strands 408 at a folding apparatus 494. As shown in FIG. 13, adhesive 497 may be applied to the single continuous substrate 400 and the continuous elastic strands 408 using an adhesive applicator 487 before advancing through the folding apparatus 494. From the folding apparatus 494, the single continuous substrate 400 and the continuous elastic strands 408 advances through a first metering device 450. The elastic material 406 is bonded to the single continuous substrate 400 to form the layered elastic substrate 420 at the first metering device 450. From the first metering device 450, the layered elastic substrate 420 advances in the machine direction MD to a second metering device 452. The layered elastic substrate 420 is consolidated between the first and second metering 450 and 452.

Figure 14:
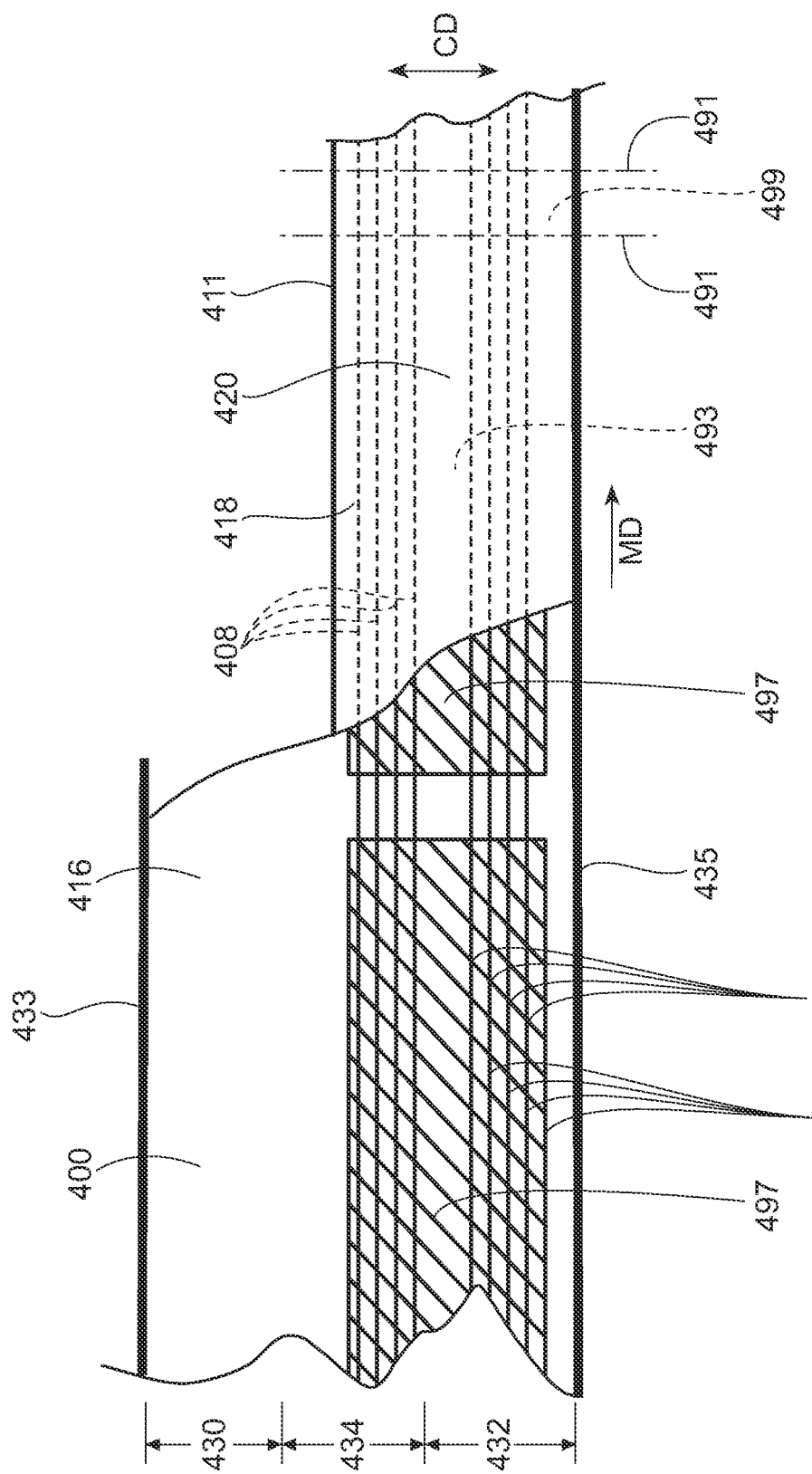
FIG. 14 is a schematic, plan view of a single continuous substrate and elastic material taken along line A-A from FIG. 13.
Figure 15:
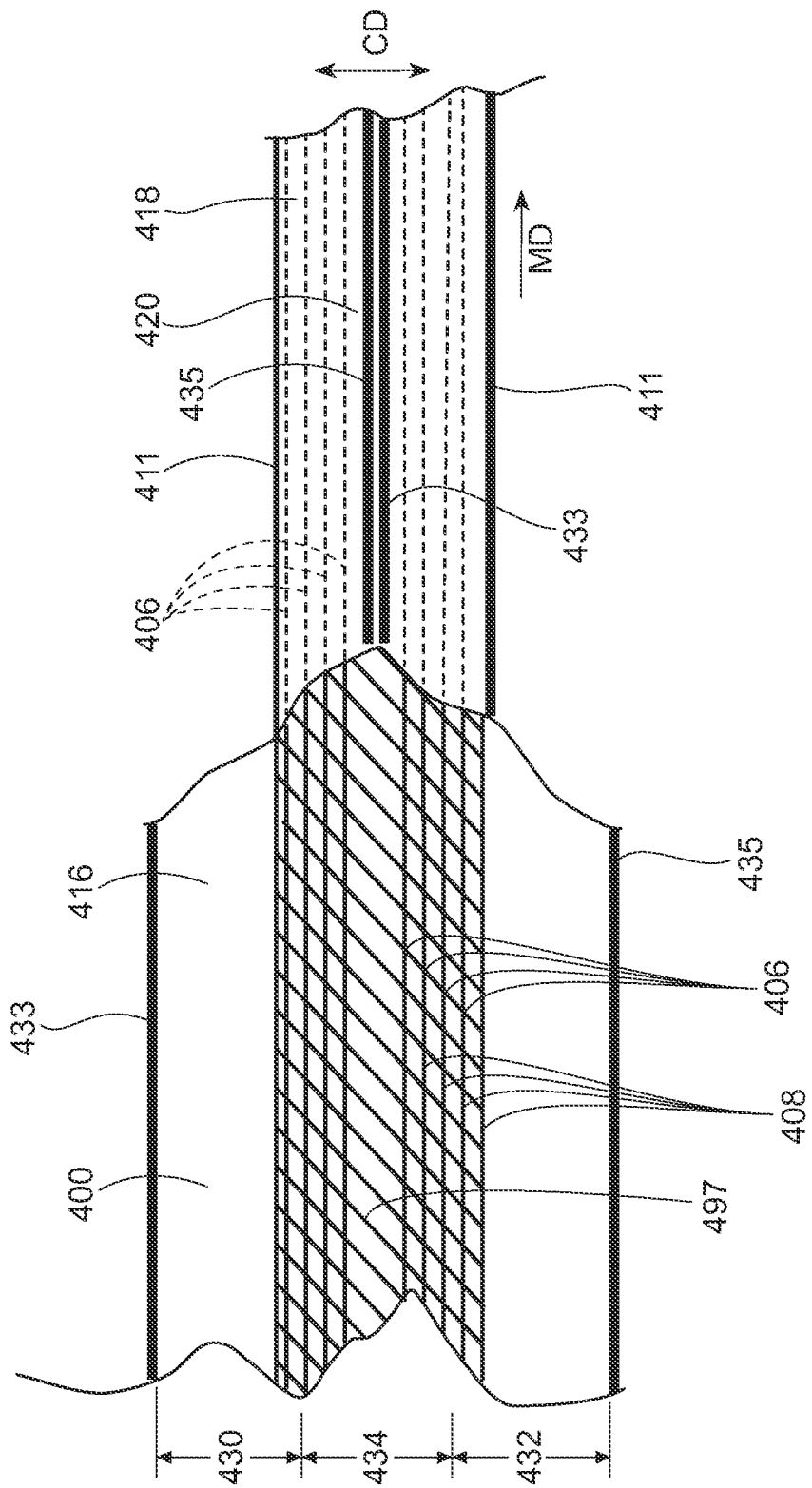
FIG. 15 is a schematic, plan view of a single continuous substrate and elastic material taken along line A-A from FIG. 13.

With continuing reference to FIG. 13, it is to be appreciated that the folding apparatus 494 may be configured to fold the single continuous substrate 400 in various ways. FIGS. 14 and 15 show two exemplary folding configurations for the single continuous substrate 400. It is to be appreciated that FIGS. 14 and 15 are alternative views taken along line A-A of FIG. 13. As shown in FIGS. 14 and 15, the single continuous substrate 400 of FIG. 13 may include a first surface 416 and an opposing second surface 418. The single continuous substrate 400 may be defined by a first edge region 430 and second edge region 432 separated along the cross direction CD by an inner region 434. In some exemplary configurations, the single continuous substrate 400 may be folded at a fold line 411 in the inner region 434 along the machine direction MD such that the first edge region 430 and the second edge region 432 of the first surface 416 are in a facing relationship such as shown in FIG. 14.

In some exemplary configurations, as shown in FIG. 15, the single continuous substrate 400 may be folded at two fold lines 411 in each of the first and second edge regions 430 and 432 in the machine direction MD such that the first surface 416 of each of the first edge region 430 and the second edge region 432 are in a facing relationship with the first surface 416 of the inner region 434. FIG. 15 shows an exemplary configuration where the first and second lateral edges 433 and 435 are overlapping such that a portion of the first surface 416 of the second edge region 432 is in a facing relationship with a portion of the second surface 418 of the first edge region 430 and portions of the first surface 416 of the first and second edge regions 430 and 432 are in a facing relationship with the first surface 416 of the inner region 434. However, the first and second lateral edges 433 and 435 may be arranged in various configurations. For example, as shown in FIG. 3D, the single continuous substrate 400 may be folded such that the first lateral edge 433 is adjacent to the second lateral edge 435, and in some embodiments, the first lateral edge 433 may abut the second lateral edge 435.

With reference to FIG. 14, in some exemplary configurations, the elastic strands 408 may be intermittently bonded to the single continuous substrate 400 to form the layered elastic substrate 420. For example, adhesive 497 (represented by cross-hatched areas) may be applied to the elastic strands 408 intermittently in the machine direction MD. In such an example, the layered elastic substrate 420 has bonded regions 493 where the elastic strands 408 is bonded to the single continuous substrate 400, the nonbonded regions 499 where the elastic strands 408 are not bonded to the single continuous substrate 400. For the purposes of clarity, dashed lines 491 are shown in FIG. 14 to represent example boundaries between the nonbonded regions 499 and the bonded regions 493 of the layered elastic substrate 420. As shown in FIG. 15, in other exemplary configurations, the continuous elastic strands 408 may be continuously bonded to the single continuous substrate 400 to form the layered elastic substrate 420. For example, adhesive 497 (represented by cross-hatched areas) may be applied continuously to the elastic strands 408 such that when it is joined with the single continuous substrate 400, it bonds to the single continuous substrate 400 continuously along the entire length of the single continuous substrate 400. In an exemplary configuration where the first substrate layer is formed from a first continuous substrate and the second substrate layer is formed from a second continuous substrate, it is to be appreciated that the elastic material may also be intermittently or continuously bonded to the first and second continuous substrates.

Referring back to FIG. 13, the first metering device 450 includes a first roller 456 having an outer circumferential surface 460 and rotates about a first axis of rotation 476 and a second roller 458 having an outer circumferential surface 462 and rotates about a second axis of rotation 478. The first roller 456 and the second roller 458 rotate in opposite directions, and the second roller 458 is adjacent the first roller 456 to define a first nip 486 between the first roller 456 and the second roller 458. The first and second rollers 456 and 458 rotate such that the outer circumferential surfaces 460 and 462 have a surface speed V1. The second metering device 452 shown in FIG. 13 includes a drum 472 having an outer circumferential surface 474 and rotates about an axis of rotation 484. The drum 472 rotates such that the outer circumferential surface 474 has a surface speed V2. The surface speed V1 may be greater than the surface speed V2 such that the layered elastic substrate 420 consolidates in the machine direction MD between the first metering device 450 and the second metering device 452 from a first elongation to a second elongation that is less than the first elongation.

Figure 16:
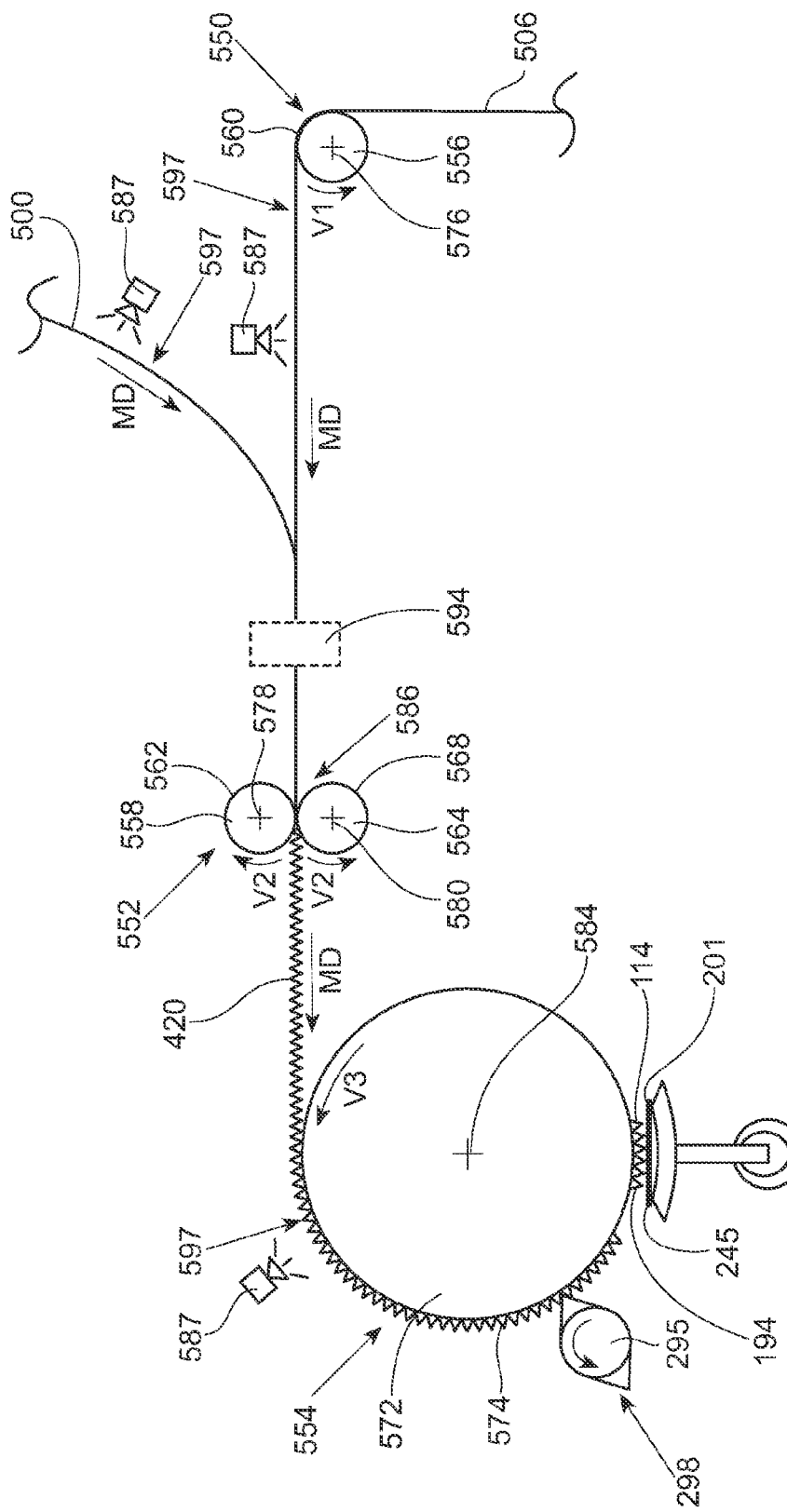
FIG. 16 is a schematic, side elevation view of an apparatus for making a layered elastic substrate, cutting the layered elastic substrate into discrete waistbands, and bonding the discrete waistbands with a continuous length of absorbent articles.

FIG. 16 shows another exemplary process assembling discrete lengths of layered elastic substrate. As shown in FIG. 16, a continuous length of elastic material 506 may be advanced in a machine direction MD to a first metering device 550. A single continuous substrate 500 is advanced in the machine direction MD. From the first metering device 550, the single continuous substrate 500 is folded over the elastic material 506 at a folding apparatus 594. Adhesive 597 may be applied to the single continuous substrate 500 and the elastic material 506 by an adhesive applicator 587 before advancing through the folding apparatus 594. From the folding apparatus 594, the continuous lengths of elastic material 506 and single continuous substrate 500 are advanced through a second metering device 552 that acts to bond the elastic material 506 to the single continuous substrate 500 to form a layered elastic substrate 520. The first and second metering devices 550 and 552 also act to stretch the advancing continuous length of elastic material 506 between the first and second metering devices 550 and 552 from a first elongation to a second elongation that is greater than the first elongation. The layered elastic substrate 520 then advances in the machine direction MD to a third metering device 554. The layered elastic substrate 520 is consolidated in the machine direction MD between the second and third metering devices 552 and 554 from a second elongation to a third elongation that is less than the second elongation and greater than the first elongation. It is to be appreciated that the folding apparatus of FIG. 16 may be configured to fold the single continuous substrate 500 in various ways, such as those described above with regard to FIGS. 13-15.

With continuing reference to FIG. 16, the first metering device 550 may include a first roller 556 having an outer circumferential surface 560 and rotates about a first axis of rotation 576. The first roller 556 rotates such that the outer circumferential surface 560 have a surface speed V1. The second metering device 552 may include a first roller 558 having an outer circumferential surface 562 and rotates about a first axis of rotation 578 and a second roller 564 having an outer circumferential surface 568 and rotates about a second axis of rotation 580. The first roller 558 and the second roller 564 rotate in opposite directions, and the second roller 564 is adjacent the first roller 558 to define a first nip 586 between the first roller 564 and the second roller 566. The first and second rollers 558 and 564 rotate such that the outer circumferential surfaces 562 and 568 have a surface speed V2. The surface speed V2 may be greater than the surface speed V1 such that the elastic material 506 stretches in the machine direction MD from a first elongation to a second elongation that is greater than the first elongation between the first metering device 550 and the second metering device 552. The third metering device 554 may include a drum 572 having an outer circumferential surface 574 and rotates about an axis of rotation 584. The drum 572 rotates such that the outer circumferential surface 574 has a surface speed V3. The surface speed V3 may be less than the surface speed V2, but greater than the surface speed V1, such that the layered elastic substrate 520 consolidates in the machine direction MD between the second and third metering devices 552 and 554, from a second elongation to a third elongation that is less than the second elongation and greater than the first elongation.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a layered elastic substrate, the method comprising the steps of:
    advancing a substrate in a machine direction, the substrate defining a first edge region and a second edge region separated by an inner region along a cross direction, the substrate having a first surface and an opposing second surface;
    advancing an elastic material in a stretched state in the machine direction;
    bonding the elastic material in the stretched state to the first surface of the substrate;
    folding the substrate to position the first surface of the first edge region into a facing relationship with the first surface of the inner region;
    folding the substrate to position the first surface of the second edge region into a facing relationship with the first surface of the inner region to form a layered elastic substrate;
    advancing the layered elastic substrate through a first metering device at speed, V1, wherein the elastic material is stretched to a first elongation at the first metering device; and
    advancing the layered elastic substrate through a second metering device at speed, V2, subsequent to advancing the layered elastic substrate through the first metering device, wherein V1 is greater than V2, and relaxing the elastic material to a second elongation between the first and the second metering devices;
    cutting the layered elastic substrate into discrete lengths of layered elastic substrates;
    holding the discrete lengths of layered elastic substrates at the second elongation, wherein each discrete length of layered elastic substrates comprises one or more gathers;
    advancing a stretched continuous length of absorbent articles in a second machine direction; and
    bonding each discrete length of layered elastic substrate at the second elongation to the stretched continuous length of absorbent articles.

2. The method of claim 1, further comprising the step of folding the substrate to position the first surface of the second edge region into a facing relationship with the second surface of the first edge region to form a layered elastic substrate.

3. The method of claim 1, wherein the elastic material comprises an elastic strand.

4. The method of claim 1, wherein the first elongation is about 150% and the second elongation is about 80%.

5. The method of claim 1, wherein the first metering device comprises a first roller rotating about a first axis of rotation, the first roller having an outer circumferential surface moving at speed, V1.

6. The method of claim 5, wherein the first metering device further comprises a second roller rotating about a second axis of rotation, the second roller having an outer circumferential surface moving at speed, V1, wherein the first roller and the second roller rotate in opposite directions, wherein the second roller is located adjacent to the first roller to define a first nip between the first roller and the second roller.

7. The method of claim 1, wherein the second metering device comprises a first roller rotating about a first axis of rotation, the first roller having an outer circumferential surface moving at speed, V2.

8. The method of claim 7, wherein the second metering device further comprises a second roller rotating about a second axis of rotation, the second roller having an outer circumferential surface moving at speed, V2, wherein the first roller and the second roller rotate in opposite directions, wherein the second roller is located adjacent to the first roller to define a second nip between the first roller and the second roller.

9. A method for making a layered elastic substrate, the method comprising the steps of:
    advancing a first substrate layer in a machine direction, having a first surface and an opposing second surface;
    advancing a second substrate layer in the machine direction, having a first surface and an opposing second surface;

advancing an elastic material in a stretched state in the machine direction;

bonding the elastic material in the stretched state to the first surface of the first substrate layer and the first surface of the second substrate layer to form a layered elastic substrate;

advancing the layered elastic substrate through a first metering device at speed, V1, wherein the elastic material is stretched to a first elongation at the first metering device; and advancing the layered elastic substrate through a second metering device at speed, V2, subsequent to advancing the layered elastic substrate through the first metering device, wherein V1 is greater than V2, and wherein the elastic material is relaxed to a second elongation between the first and second metering devices;

cutting the layered elastic substrate into discrete length of layered elastic substrate, wherein each discrete length of layered elastic substrate comprise a first end portion, a second end portion, and an inner portion between the first end portion and the second end portion;

holding at least one of the first end portion, the second end portion, and the inner portion of the discrete length of layered elastic substrate at the second elongation and relaxing at least one of first end portion, the second end portion, and the inner portion of the discrete length of layered elastic substrate;

advancing a stretched continuous length of absorbent articles in a second machine direction; and bonding each discrete length of layered elastic substrate to the stretched continuous length of absorbent articles.

10. The method of claim 9, wherein the elastic material comprises an elastic strand.

11. The method of claim 9, wherein the elastic material comprises an elastic film.

12. The method of claim 9, wherein the first elongation is about 150% and the second elongation is about 80%.

13. The method of claim 9, wherein the first metering device comprises a first roller rotating about a first axis of rotation, the first roller having an outer circumferential surface moving at speed, V1.

14. The method of claim 13, wherein the first metering device further comprises a second roller rotating about a second axis of rotation, the second roller having an outer circumferential surface moving at speed, V1, wherein the first roller and the second roller rotate in opposite directions, wherein the second roller is located adjacent the first roller to define a first nip between the first roller and the second roller.

15. The method of claim 9, wherein the second metering device comprises a first roller rotating about a first axis of rotation, the first roller having an outer circumferential surface moving at speed, V2.

16. The method of claim 15, wherein the second metering device further comprises a second roller rotating about a second axis of rotation, the second roller having an outer circumferential surface moving at speed, V2, wherein the first roller and the second roller rotate in opposite directions, wherein the second roller is located adjacent the first roller to define a second nip between the first roller and the second roller.

17. The method of claim 9, further comprising the steps of:
cutting the continuous length of web material along an inner region of each discrete length of layered elastic substrate to separate the continuous length of web material into discrete diapers.

18. The method of claim 9, further comprising the steps of:
advancing a single continuous substrate having a first surface and an opposing second surface in the machine direction, and defining a width in a cross direction, wherein the single continuous substrate includes opposing first and second lateral edges and longitudinally opposed first and second edge regions separated along the cross direction by an inner region; and forming the first and second substrate layers by folding the first surface of the first edge region of the single continuous substrate onto a portion of the first surface of either the first edge region, the inner region, or the second edge region of the single continuous substrate.

19. The method of claim 9, wherein the step of bonding the elastic material further comprises intermittently bonding the elastic material.

20. A method for making a layered elastic substrate, the method comprising the steps of:
advancing a first substrate in a machine direction, having a first surface and an opposing second surface;
advancing a second substrate in the machine direction, having a first surface and an opposing second surface;
advancing an elastic material in a stretched state in the machine direction;
bonding the elastic material in the stretched state to the first surface of the first substrate and the first surface of the second substrate to form a layered elastic substrate;
stretching the elastic material to a first elongation at a first metering device; and
consolidating the elastic material to a second elongation between the first metering device and a second metering device;
cutting the layered elastic substrate into discrete lengths of layered elastic substrate, the discrete lengths of layered elastic substrate define a first edge region and a second edge region separated along the cross direction by an inner region;
holding the discrete lengths of layered elastic substrate to maintain the second elongation along a length of the discrete lengths of layered elastic substrate;
advancing a continuous length of web material in a second machine direction, wherein the continuous length of web material is stretched; and
bonding each discrete length of layered elastic substrate at the second elongation to the continuous length of web material wherein the discrete lengths of layered elastic substrate are spaced apart from each other along the second machine direction.

21. The method of claim 20, further comprising the step of:
cutting the continuous length of web material along the inner region of each discrete length of layered elastic substrate to separate the continuous length of web material into discrete diapers.

22. The method of claim 21, wherein each discrete length of layered elastic substrate defines a first end portion and a second end portion separated by an inner portion, and further comprising the step of:
further consolidating the first end portion of each discrete length of layered elastic substrate.

23. The method of claim 21, wherein each discrete length of layered elastic substrate defines a first end portion and a second end portion separated by an inner portion, and further comprising the step of:
further consolidating the inner portion of each discrete length of layered elastic substrate.

24. The method of claim 21, wherein each discrete length of layered elastic substrate defines a first end portion and a second end portion separated by an inner portion, and further comprising the step of:
   allowing the first end portion of each discrete length of layered elastic substrate to relax.

25. The method of claim 20, wherein the elastic material is intermittently bonded in the stretched state to the first surface of the first substrate and the first surface of the second substrate to form a layered elastic substrate with bonded regions and nonbonded regions; and
   wherein the layered elastic substrate is cut along the nonbonded regions into discrete lengths of layered elastic substrate such that the elastic material cut along the nonbonded regions retracts to the bonded regions, wherein the discrete lengths of layered elastic substrate define a first end portion and a second end portion separated in the machine direction by an inner portion, wherein no elastic material is located in the first and second end portions.

26. The method of claim 21, further comprising the steps of:
   advancing the layered elastic substrate through a first metering device at speed, V1; and
   advancing the layered elastic substrate through a second metering device at speed, V2, subsequent to advancing the layered elastic substrate through the first metering device, wherein V1 is greater than V2.

* * * * *